(12) United States Patent
Pepper et al.

(10) Patent No.: US 9,480,576 B2
(45) Date of Patent: Nov. 1, 2016

(54) METHODS AND SYSTEMS FOR INTERBODY IMPLANT AND BONE GRAFT DELIVERY

(75) Inventors: John R. Pepper, Chesire, CT (US); Daniel K. Farley, Traverse City, MI (US); Christopher T. Martin, Empire, MI (US); Stephanie Zalucha, Williamsburg, MI (US); Miguelangelo J. Perez-Cruet, Bloomfield, MI (US)

(73) Assignee: THOMPSON MIS, Salem, NH (US)

( * ) Notice: Subject to any disclaimer, the term of this patent is extended or adjusted under 35 U.S.C. 154(b) by 745 days.

(21) Appl. No.: 13/614,393

(22) Filed: Sep. 13, 2012

(65) Prior Publication Data

US 2013/0006365 A1 Jan. 3, 2013

Related U.S. Application Data

(63) Continuation-in-part of application No. 13/182,947, filed on Jul. 14, 2011, now abandoned.

(60) Provisional application No. 61/377,691, filed on Aug. 27, 2010.

(51) Int. Cl.
*A61F 2/44* (2006.01)
*A61F 2/46* (2006.01)
*A61F 2/30* (2006.01)

(52) U.S. Cl.
CPC .............. *A61F 2/447* (2013.01); *A61F 2/4611* (2013.01); *A61F 2/30965* (2013.01);
(Continued)

(58) Field of Classification Search
CPC .. A61F 2/4611; A61F 2/4455; A61F 2/4601; A61F 2/442; A61F 2002/2835; A61F 2002/30112; A61F 2002/4624; A61F 2002/4649; A61F 2220/0025; A61F 2002/3008; A61F 2002/30166; A61F 2002/30235; A61F 2002/30367; A61F 2002/30426; A61F 2002/3082; A61F 2002/4627; A61F 2002/4629; A61F 2220/0033; A61M 2210/02; A61M 5/24; A61M 5/28; A61B 2017/0256; A61B 17/1671; A61B 17/1757; A61B 17/88
USPC .................. 604/285; 606/279, 92; 623/17.16
See application file for complete search history.

(56) References Cited

U.S. PATENT DOCUMENTS 4,061,453 A * 12/1977 DeSantis ................. B30B 11/04
425/352
4,874,368 A 10/1989 Miller
(Continued)

FOREIGN PATENT DOCUMENTS

WO WO2005/016783 A1 2/2005
WO WO2005/060367 A2 7/2005

OTHER PUBLICATIONS

PCT, Notification of Transmittal of International Preliminary Report on Patentability, in International Application No. PCT/US11/49371, Jan. 24, 2013 (65 pages).
(Continued)

*Primary Examiner* — Bhisma Mehta
*Assistant Examiner* — Brandy S Lee
(74) *Attorney, Agent, or Firm* — McAndrews, Held & Malloy, Ltd.

(57) ABSTRACT

A bone graft system for providing bone graft material to a site of interest includes a multiple unit bone graft material loading device and a conduit. The multiple unit bone graft material loading device may be configured to accept a plurality of pre-formed bone graft material units and includes a plurality chambers configured to accept a pre-formed bone graft unit. The conduit may include a first opening and second opening. The first opening may be operably connected with the multiple unit bone graft material loading device to accept bone graft material from the multiple unit bone graft material loading device. The second opening may be configured to deliver bone graft material to a site of interest.

18 Claims, 14 Drawing Sheets

(52) U.S. Cl.
CPC .......... *A61F 2/4465* (2013.01); *A61F 2/4644* (2013.01); *A61F 2002/305* (2013.01); *A61F 2002/3008* (2013.01); *A61F 2002/3083* (2013.01); *A61F 2002/30266* (2013.01); *A61F 2002/30281* (2013.01); *A61F 2002/30616* (2013.01); *A61F 2002/30825* (2013.01); *A61F 2002/30828* (2013.01); *A61F 2002/30843* (2013.01); *A61F 2002/30892* (2013.01); *A61F 2002/4627* (2013.01); *A61F 2002/4628* (2013.01); *A61F 2310/00017* (2013.01); *A61F 2310/00023* (2013.01); *A61F 2310/00359* (2013.01); *A61F 2310/00407* (2013.01); *A61F 2310/00574* (2013.01); *A61F 2310/00958* (2013.01)

(56) References Cited

U.S. PATENT DOCUMENTS

| | | |
|---|---|---|
| 6,616,593 B1 | 9/2003 | Elliott |
| 6,620,185 B1 | 9/2003 | Harvie |
| 2002/0160032 A1* | 10/2002 | Long .................. A61F 2/28 424/423 |
| 2003/0014116 A1 | 1/2003 | Ralph |
| 2003/0236573 A1 | 12/2003 | Evans |
| 2004/0097829 A1* | 5/2004 | McRury ............ A61B 10/0266 600/564 |
| 2006/0085008 A1 | 4/2006 | Jaggi |
| 2007/0282441 A1 | 12/2007 | Stream et al. |
| 2008/0154377 A1 | 6/2008 | Voellmicke |
| 2008/0172128 A1* | 7/2008 | Perez-Cruet .......... A61F 2/4611 623/17.16 |
| 2008/0260598 A1 | 10/2008 | Gross |
| 2009/0137946 A1 | 5/2009 | Nassiri |
| 2012/0277754 A1 | 11/2012 | Lin et al. |

OTHER PUBLICATIONS

Patent Cooperation Treaty, Notification of Transmittal of the International Search Report and the Written Opinion of the International Searching Authority, or the Declaration, in International Application No. PCT/US11/49377, dated Dec. 23, 2011 (12 pages).
Patent Cooperation Treaty, Notification of Transmittal of the International Search Report and the Written Opinion of the International Searching Authority, or the Declaration, in International Application No. PCT/US11/49371, dated Jan. 19, 2012 (13 pages).
PCT International Preliminary Report on Patentability, in International Application No. PCT/US11/49371, Oct. 11, 2012 (55 pages).
European Patent Office, Communication pursuant to Rules 70(2) and 70a(2) EPC, in Application No. 11820735.6, dated Feb. 7, 2014.
European Patent Office, Communication with extended European search report, in Application No. 11820735.6, dated Jan. 21, 2014.

* cited by examiner

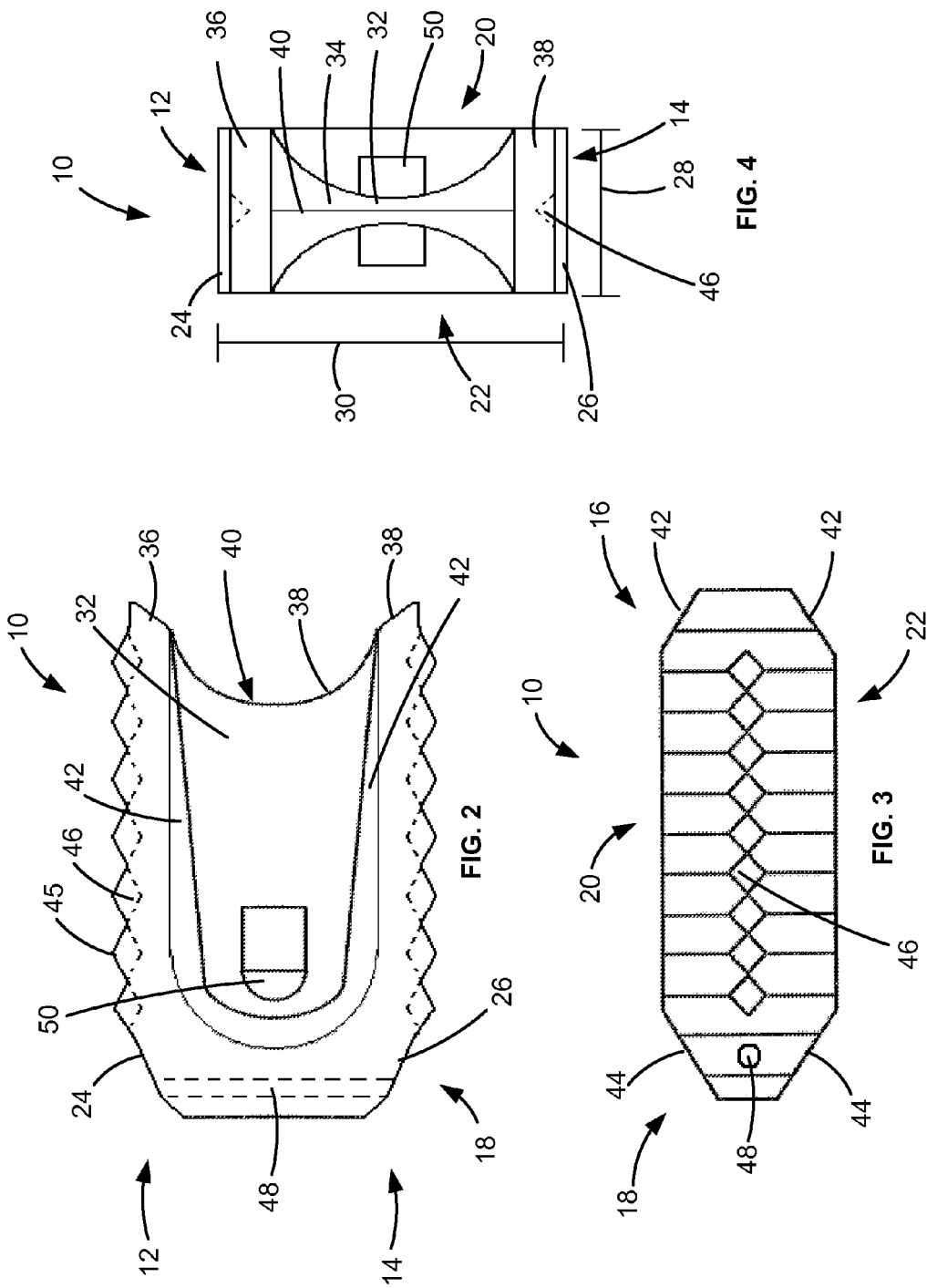

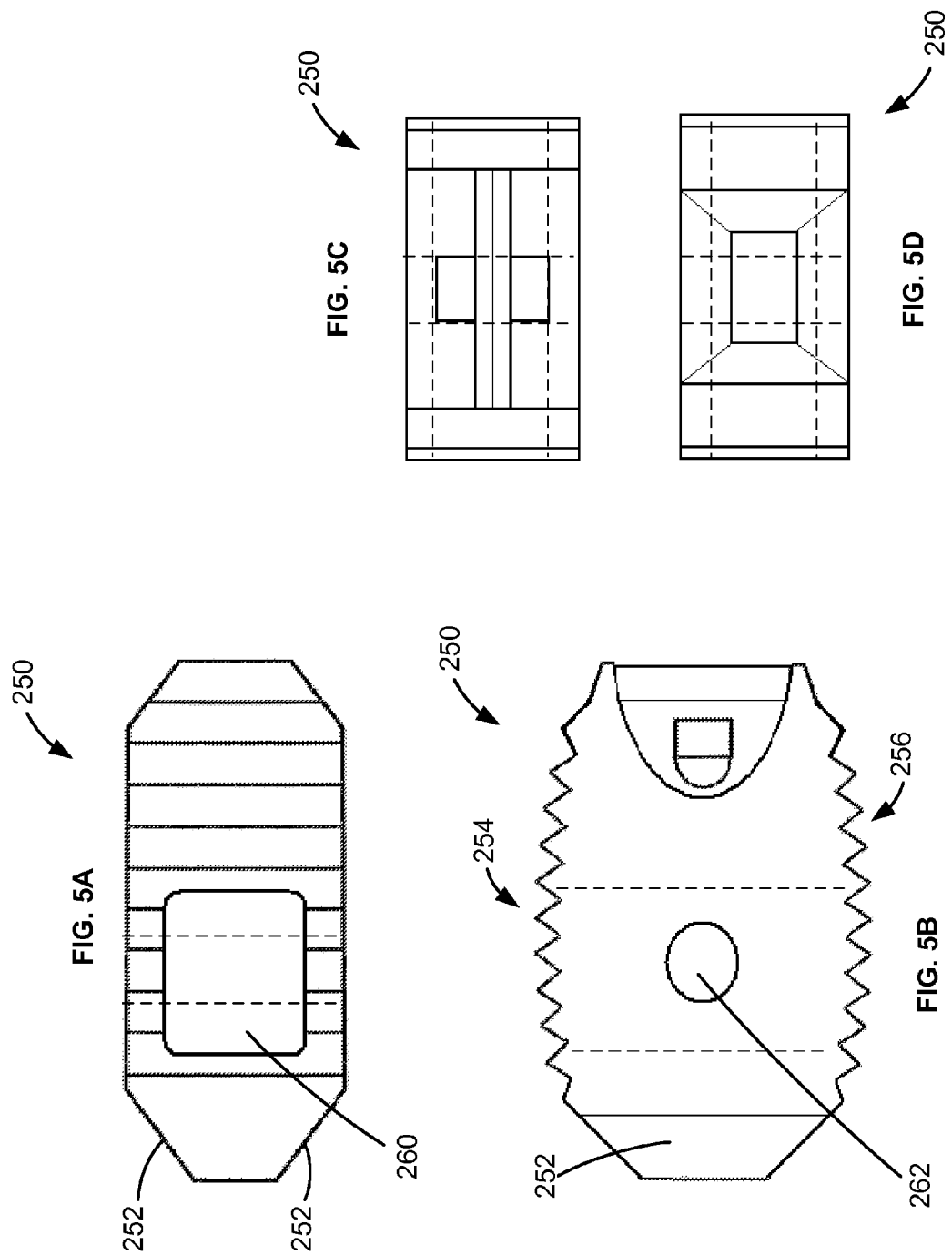

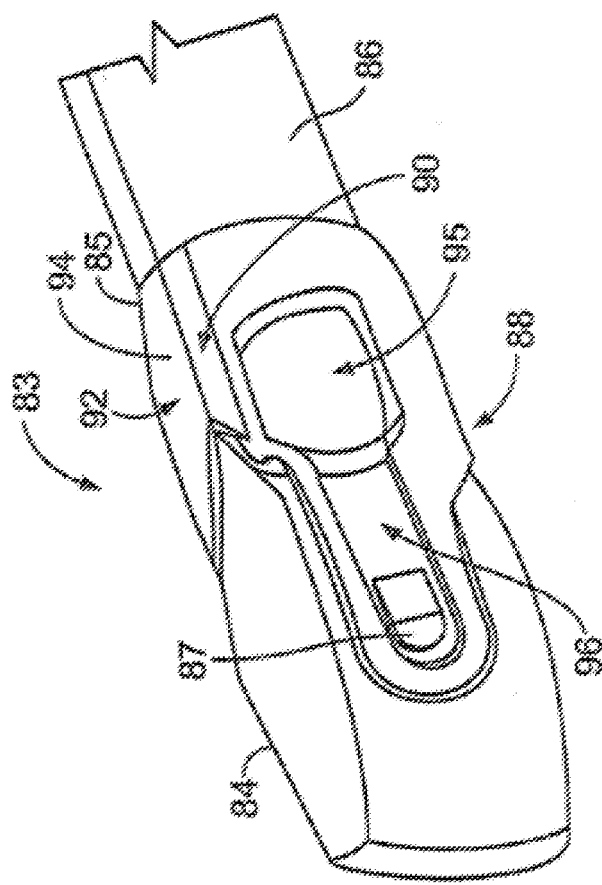

METHODS AND SYSTEMS FOR INTERBODY IMPLANT AND BONE GRAFT DELIVERY

CROSS-REFERENCE TO RELATED APPLICATION

This application is a continuation-in-part, and claims priority to, U.S. patent application Ser. No. 13/182,947, filed Jul. 14, 2011, which claims priority to U.S. Provisional Patent Application No. 61/377,691, filed Aug. 27, 2010. The entire contents of these two applications are hereby incorporated by reference in their entireties.

BACKGROUND OF THE INVENTION

The present invention relates to systems and methods for providing spinal implants, for example, to be used in connection with spinal fusion.

Spinal fusion is a surgical procedure that fuses two or more vertebrae together using bone graft materials supplemented with devices. Spinal fusion may be performed for the treatment of chronic neck and/or back pain, trauma, and neoplasms. Spinal fusion can be used to stabilize and eliminate motion of vertebrae segments that may be unstable, or move in an abnormal way, that can lead to discomfort and pain. Spinal fusion may be performed to treat injuries to the vertebrae, degeneration of spinal discs, abnormal spinal curvature, and/or a weak or unstable spine.

Spinal fusion generally requires a graft material, usually bone material, to fuse the vertebrae together. The bone graft material can be placed over the spine to fuse adjacent vertebrae together. Alternatively, a device (i.e. cage) may be positioned between the vertebrae being fused and filled with the bone graft material. Such a cage can include holes that allow the vertebrae and the graft material to grow together to provide fusion, with the cage supporting the weight of the vertebrae while the fusion is occurring. Most of these cages are limited to only a few cubic centimeters of bone graft material thus limiting the fusion area achieved. Because the fusion mass is under pressure, fusion can be promoted. The disc space height can be restored, taking pressure off of the nerves. The spine alignment, foraminal height, and canal diameter can be restored. In some cases the graft can be placed with minimal disruption of muscles and ligaments using minimally invasive approaches to the spine, thus preserving the normal anatomical integrity of the spine. Other interbody device assemblies are also presently known. These include those disclosed in U.S. patent application Ser. No. 11/623,356, filed Jan. 16, 2007, titled "Minimally Invasive Interbody Device," and Ser. No. 11/932,175, filed Oct. 31, 2007, titled "Minimally Invasive Interbody Device Assembly," which are hereby incorporated by reference in their entirety.

Typically, the bone graft material is autogenous bone material taken from the patient, or allograft bone material harvested from a cadaver. Synthetic bone material can also be used as the graft material. Generally, the patient's own bone material offers the best fusion material since it offers osteoinductive, osteoconductive, and osteogenesis properties. Known bone fusion materials include iliac crest harvest from the patient, bone graft extenders, such as hydroxyapetite and demineralized bone matrix, and bone morphogenic protein.

Minimally invasive surgical procedures have been devised in an attempt to preserve normal anatomical structures during spinal surgery. Many known procedures for spinal fusion, however, still are more invasive than desired. Additionally, many known procedures do not provide the level of control over the delivery and placement of the bone graft material as could be desired. Additionally, current interbody devices only allow for a limited application of bone material (i.e., cages), and because of their relative size place the neural elements at risk during placement, often resulting in undersized implants being placed.

It is therefore one object of the present invention to provide a spinal implant system that reduces approach related morbidity, allows for more bone graft placement and/or provides improved control of the delivery and/or placement of bone graft material.

BRIEF SUMMARY OF THE INVENTION

These and other objects of the invention are achieved, in certain embodiments, in a spacer for implantation between adjacent vertebrae. The spacer includes a distal end and a proximal end. The spacer also includes top and bottom surfaces spaced by sides. The top and bottom surfaces define a height, and the sides define a width. In certain embodiments, the height is greater than the width, wherein the spacer may be inserted with its sides oriented toward surfaces of adjacent vertebrae and then rotated into place with the top and bottom surface oriented toward the surfaces of the adjacent vertebrae to maintain a desired space between the adjacent vertebrae. In such an application of the device, nerve root retraction can be reduced and improved disc height restoration achieved. The sides of the spacer may include depressed regions sunk into the side (for example a cutouts) that define a web which may include one or more surfaces, for example surfaces that slope, at least toward the proximal end of the spacer. In one example, the distance between the surfaces of the web may decrease proximally to form a wedge having a leading edge proximate to the proximal end of the spacer. The surface(s) may be sized and configured to aid distribution or disbursement of bone graft material to either side of the spacer, wherein bone graft material may be supplied to a site of interest and distributed to at least one side of the spacer. Thus, the interbody device may be placed, in certain embodiments rotated to restore disc height, and bone then passed on either side of the implant allowing for better and more bone graft delivery into the disc interspace. The feed reservoir defines a passageway through which bone graft material may be delivered to the spacer when the spacer is positioned as desired between adjacent vertebrae. The feed reservoir includes an alignment feature configured to align the feed reservoir with the spacer so that bone graft material delivered to the spacer through the feed reservoir is distributed to at least one side of the web of the spacer. The plunger is configured to be accepted by the passageway of the feed reservoir, and is configured to help advance bone graft material along a length of the feed reservoir.

Certain embodiments of the present invention provide a bone graft system for providing bone graft material to a site of interest. The system includes a bone graft container, such as a cartridge, and a conduit. The bone graft cartridge is configured to accept bone graft material. In certain embodiments, the bone graft cartridge comprises a top half and a bottom half that may be moved between an open and closed position. The conduit has a first opening and a second opening. The first opening is sized and configured to accept the bone graft cartridge, and the second opening is configured to deliver bone graft material to a site of interest.

The system may also include an inserter and a spacer. In certain embodiments, the inserter includes a gripping portion for grasping the spacer, with the conduit formed in the interior of the inserter. The bone graft cartridge is inserted into the inserter and bone graft material is delivered proximate to the spacer.

In certain embodiments, the bone graft cartridge and the first opening of the conduit include cooperating sloped surfaces to limit the depth to which the bone graft cartridge may be inserted into the conduit.

Certain embodiments of the present invention provide a bone graft system for providing bone graft material to a site of interest that includes a multiple unit bone graft material loading device and a conduit. The multiple unit bone graft material loading device is configured to accept a plurality of pre-formed bone graft material units and includes a plurality of chambers configured to accept a pre-formed bone graft unit. In certain embodiments, the multiple unit bone graft material loading device comprises a carousel, with the plurality of chambers arranged in a circular arrangement disposed in the carousel. The conduit includes a first opening and second opening. The first opening is operably connected with the multiple unit bone graft material loading device to accept bone graft material from the multiple unit bone graft material loading device. The second opening is configured to deliver bone graft material to a site of interest.

Certain embodiments of the present invention provide a method of providing bone graft material to a site of interest. The method includes forming bone graft material into a predetermined size and shape configured to be accepted by a conduit, and positioning the conduit with a distal end of the conduit proximate to a site of interest. The method also includes inserting the bone graft material of the predetermined size and shape into an opening of the conduit and advancing the bone graft material through the conduit to the site of interest.

BRIEF DESCRIPTION OF THE SEVERAL VIEWS OF THE DRAWINGS

FIG. 2 illustrates a side view of the spacer of FIG. 1.

FIG. 3 illustrates a top view of the spacer of FIG. 1.

FIG. 4 illustrates an end view (looking from the proximal end) of the spacer of FIG. 1.

FIG. 5A illustrates a top view of a spacer, formed in accordance with an embodiment of the present invention.

FIG. 5B illustrates a side view of the spacer of FIG. 5A.

FIG. 5C illustrates an end view (looking from the proximal end) of the spacer of FIG. 5A.

FIG. 5D illustrates an end view (looking form the distal end) of the spacer of FIG. 5A.

FIG. 7 illustrates a perspective view of an implant system including an inserter joined to a spacer formed in accordance with an embodiment of the present invention.

DETAILED DESCRIPTION

Figure 1:
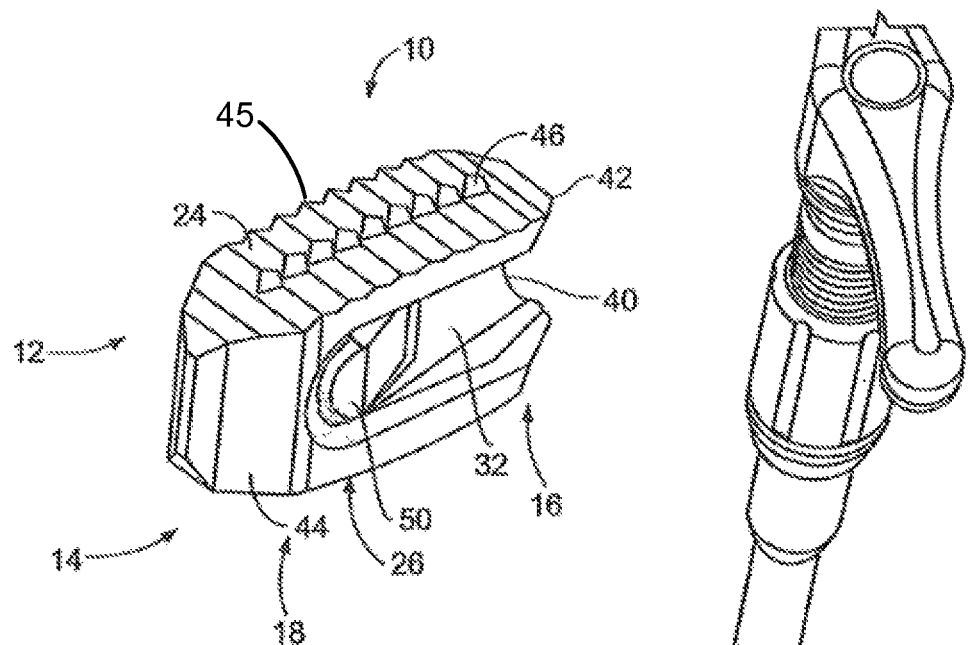
FIG. 1 illustrates a perspective view of a spinal implant, or spacer, formed in accordance with an embodiment of the present invention.

FIG. 1 illustrates a perspective view of a spinal implant, or spacer, 10; FIG. 2 illustrates a side view of the spacer 10; FIG. 3 illustrates a top view of the spacer 10; and FIG. 4 provides an end view (looking from the proximal end) of the spacer 10. The spacer 10 is sized and adapted to maintain a desired spatial relationship between adjacent vertebrae. Different sizes of spacers are used to accommodate different procedures and/or sizes of patient anatomy. The spacer 10 may, for example, be made of PEEK (polyether ether ketone), titanium, carbon fiber, bone allograft, or a plurality of materials. The spacer 10 may, for example, be solid in certain embodiments, and, in other embodiments, include a hollow portion or portions. The spacer 10 includes a top side 12 and a bottom side 14. (The spacer 10 illustrated in FIGS. 1-4 is symmetric, so "top" and "bottom" sides may be interchangeable). Alternatively, the spacer can be of greater height distally to allow for lordotic disc height restoration. The spacer 10 also includes a proximal end 16 and a distal end 18. The proximal end 16 is the end of the spacer 10 designed to be located closer to a practitioner during a procedure, and the distal end 18 is the end of the spacer 10 designed to be oriented more deeply inside a patient during a procedure. The spacer 10 also includes sides 20, 22. The top side 12 includes a top surface 24 and the bottom side 14 includes a bottom surface 26. The spacer 10 defines a width 28 that is substantially less than its height 30 (with the height being defined by the distance between the top surface 24 and bottom surface 26, and the width defined by the distance between the sides 20, 22). A cutout 32 is cut into each side proximate to the proximal end 16. Cutouts are an example of a depressed region sunk into the surface of the sides. The cutouts may be formed by removing material from the sides, but may be formed in alternate fashion as well, such as, for example, a molding process. In the illustrated embodiment, the cutout 32 includes a semi-circular edge proximate to its proximal end. In alternate embodiments, the shape of the cutout may be different at its proximal end. For example, the proximal end of the cutout may define a substantially vertical line.

As best seen in FIGS. 2 and 4, the cutouts 32 help define a web 34, a top cap 36, and bottom cap 38. The top cap 36 and bottom cap 38 help form part of the top side 12 and bottom side 14, respectively. In the illustrated embodiment, the cutouts 32 are rounded as seen from the proximal end 16. In alternate embodiments, the cutouts 32 may define a plurality of different shapes, such as, for example, generally perpendicular (see also FIG. 6A). The web 34 may include one or more surfaces, for example two surfaces located on opposite sides of the web. The surfaces of the web 34 may act to help distribute or disperse bone graft material to either side of the spacer 10 as bone graft material is supplied to the site of interest. In some embodiments, the depth of the cutouts 32 into the sides 20, 22 increases proximally along at least a portion of the length of the cutout. Put another way, the web 34 may include one or more surfaces that slope inward (toward each other) proximally so that the distance between the sloped surfaces decreases proximally. In certain embodiments, the depth of the cutouts 32 may increase along the length of the entire cutout. In certain other embodiments, the depth may be constant for a portion of the cutout resulting in a generally flat surface having zero slope (and generally constant thickness of the web along that portion of the cutout), and then slope inwardly toward the proximal end at an intermediate point along the length of the cutout. In still other embodiments, multiple sloped surfaces having different slopes may be formed.

Thus, in some embodiments, the thickness of the web 34 (or the distance between the surfaces of the web) may decrease proximally along at least a length of the web 34 In these embodiments, the web 34 may be seen as forming a wedge 40, with the sharper portion of the wedge 40 oriented proximally. The tip of the wedge may, for example, define a generally sharp point. In other embodiments, the tip of the wedge may be blunt, rounded, or define a narrow flat surface. The wedge 40 may act to help distribute or disperse bone graft material to either side of the spacer 10 as bone graft material is supplied to the site of interest. In the illustrated embodiment, the web 34 and caps 36, 38 define generally distinct shapes toward the proximal end 16, but the cutout does not extend through the distal end 18, and the distal end 18 is a generally solid mass.

In certain embodiments, such as the embodiments depicted in FIGS. 5A-5D, the spacer may not be a generally solid mass. For example, in certain embodiments, a spacer 250 may include provisions for allowing bone graft material into and/or through additional portions of the spacer. For example, in certain embodiments, one or more holes 260 extending through the spacer between and through the top and bottom surfaces, and/or one or more holes 262 extending through the spacer between and through the sides, may be located, for example, distal of the cutouts, to provide for the inclusion of bone graft material through the spacer in communication with vertebral surfaces. The dotted lines shown in FIGS. 5A-5D may help to show that holes 260, 262 may extend through the body of the spacer, for example with two holes extending in perpendicular directions and perhaps intersecting.

The caps 36, 38 may also define surfaces 42 that taper in width to become narrower toward the proximal end 16 of the spacer 10, as seen in FIGS. 2 and 3 for example. In certain alternate embodiments, the cutout may run along the height of the spacer, thereby forming a continuous inwardly sloping surface, instead of defining generally distinct caps and a web.

Referring to FIG. 2, in the illustrated embodiment, the web 34 has a circular or crescent-shaped profile when viewed from the sides. In alternate embodiments, other configurations or shapes may be employed. For example, the profile could appear as a series of line segments instead of a continuous curve. As another example, the web 34, when viewed from the side as in FIG. 2, may define a generally vertical line extending from at or near the proximal edge of the top cap 36 to the bottom cap 38. Such a web may be advantageous with generally smaller spacers that use feed reservoirs having smaller cross-sectional areas. In still other embodiments, the web may have a similar vertical shape at its edge, but the edge of the web may be offset from the proximal edge of the spacer. Thus, the web need not be precisely at the proximal edge of the spacer, but may, for example, be located appropriately at other locations proximate to the proximal end of the spacer.

Figure 1A:
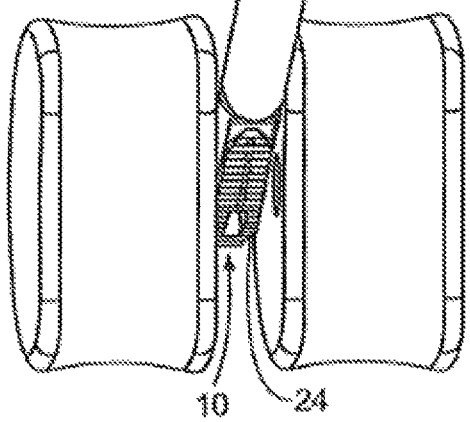
FIG. 1A illustrates a perspective view of a spinal implant being inserted between two vertebrae in a horizontal orientation.
Figure 1B:
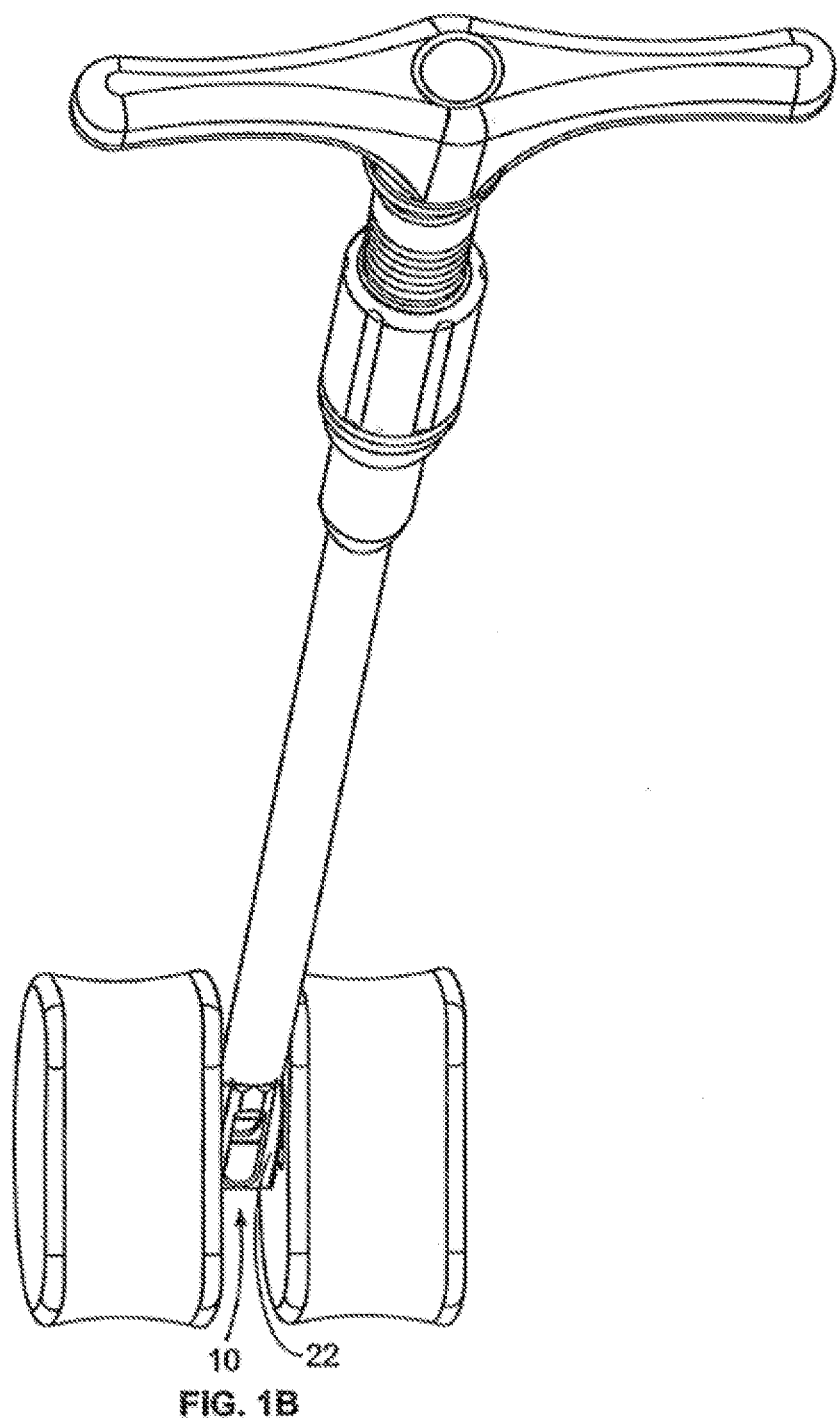
FIG. 1B illustrates a perspective view of a spinal implant rotated to its vertical position between two vertebrae.

FIG. 1A illustrates a perspective view of a spacer being inserted in a first orientation between two vertebrae, and FIG. 1B illustrates the spacer between the two vertebrae after being rotated to a second orientation to distract the vertebrae. The height 30 of the spacer 10 is selected to provide support between adjacent vertebrae. To place the spacer 10 in a patient, the spacer 10 is first inserted with its height oriented horizontally between the desired vertebrae, as shown in FIG. 1A (put another way, an axis defined by a line drawn perpendicularly through the top and bottom surfaces 24, 26 is generally perpendicular to the spine). Oriented thus, in what is referred to herein as the horizontal orientation, the spacer 10 may be inserted between the vertebrae with clearance between the spacer and the vertebrae. Then, once in place between the desired vertebrae, the spacer 10 is rotated so that its top surface 24 abuts against the bottom of the higher of the vertebrae to be fixed, and its bottom surface 26 abuts against the top of the lower of the vertebrae to be fixed, and the vertebrae are distracted, as shown in FIG. 1B. In this position, referred to herein as the vertical orientation, the spacer 10 has a sufficient height and rigidity to position and/or support the vertebrae in a desired spatial relationship to each other. For example, a spacer with height of about 11 millimeters and a width of about 7 millimeters may be placed between vertebrae spaced about 7 millimeters apart, and then rotated to its vertical position to space the vertebrae about 11 millimeters apart, thereby providing about 4 millimeters of distraction.

Regarding spacers, the top and bottom surfaces (for example surfaces 24, 26) may be straight or they may be curved so that a height across a central portion of the surfaces is greater than a height across an end portion of the surfaces. The top and bottom surfaces of the spacer illustrated in FIGS. 1-4 are substantially straight with no curve or a slight curve. The spacers 250, 11 illustrated in FIGS. 5B and 6A may be of a style that has curved top and bottom surfaces. The dimensions of the curve of the top and bottom surfaces may be selected to correspond to the shape of the vertebral surfaces to be engaged.

Referring to FIGS. 1-4, the surfaces 24, 26 may include ridges (for example, ridges 45) to help secure the spacer 10 in place between vertebrae. Surfaces 24, 26 may also include features (for example, features 46) to help secure the spacer 10 in place between vertebrae. Ridges may take the form of accordion-style peaks and valleys, although other embodiments may include other styles and shapes of raised and lowered sections to enhance grip. The features may take the form of a series of crevasses into the surfaces 24, 26. In the illustrated embodiment, the features 46 include a number of uniform pyramid-shaped crevasses arranged in a line along a central portion of surface 24 extending from distal end 18 to proximal end 16. In alternate embodiments, such pyramid-shaped crevasses may form a grid or array, or other features such as ridges, or other shapes of crevasses and or other materials may be used.

The illustrated spacer 10 also includes a radio-opaque marker 48 located proximal to the distal end 18. This marker can extend on the distal end 18 from top 24 to bottom 26. Alternative, the marker can extend from one side 20 to side 22. Additional radio-opaque markers can be placed on the proximal portion 16 of the spacer 10. These markers can be made from a plurality of radio-opaque materials. The marker (s) 48 is designed to allow the use of fluoroscopy to confirm the positioning of the spacer 10 during a procedure.

The sides 20, 22 of the spacer 10 illustrated in FIGS. 1-4 also include tapered surfaces 44 proximal to the distal end 18 (also seen in surfaces 252 of FIGS. 5A and 5B). These tapered surfaces, for example surfaces 44, form a leading edge, or bullet nose, to help ease insertion of the spacer 10 into an incision in the disc space and between vertebrae. For example, when the spacer 10 is introduced between vertebrae in its horizontal orientation, the leading portion formed by the tapered surfaces 44 provides a smaller cross-section to be inserted between the vertebrae.

The spacer 10 may also include additional features to help secure and/or align the spacer 10 with, for example, an inserter used to position the spacer and/or a funnel used to provide bone graft material to desired locations around the spacer 10. In the illustrated embodiment, the spacer 10 includes mounting buttons 50 extending from a portion of the cutout of each side for attaching an inserter to the spacer 10. The buttons 50 are sized and positioned to accept slots of the inserter, as also discussed below. In alternate embodiments, a spacer may include, for example, holes sunk into each side, with the holes being sized and positioned to accept pins protruding from a surface of the inserter, or a plurality of shapes to hold the spacer 10 during insertion.

In certain embodiments, a spacer is positioned using an inserter. Once positioned, the spacer is released by the inserter, which is then removed. A feed reservoir, such as a funnel, is then introduced to provide bone graft material to the site of interest around the spacer. In other embodiments, the feed reservoir may be incorporated in the inserter. In certain embodiments, a funnel may be aligned and/or secured to a spacer by mating one or more features on the funnel (such as a hole or slot, for example) to one or more of features of the spacer that were also used to secure the inserter to the spacer (such as a pin or button, for example). As may be further appreciated in connection with the below discussion of funnels, in alternate embodiments, the spacer may include a separate feature to help align the funnel. For example, a portion of the web of the spacer may be accepted by a v-shaped notch in the funnel. In certain embodiments, the caps may be aligned with an opening in the funnel. As an example of an additional alternative, one or more of the caps may include an alignment feature, such as a tab or wedge, that corresponds to a corresponding alignment feature, such as a slot or a notch, on the funnel. In certain embodiments, the funnel and inserter are made of stainless steel, which allows them to be sterilized and re-used.

Figure 6B:
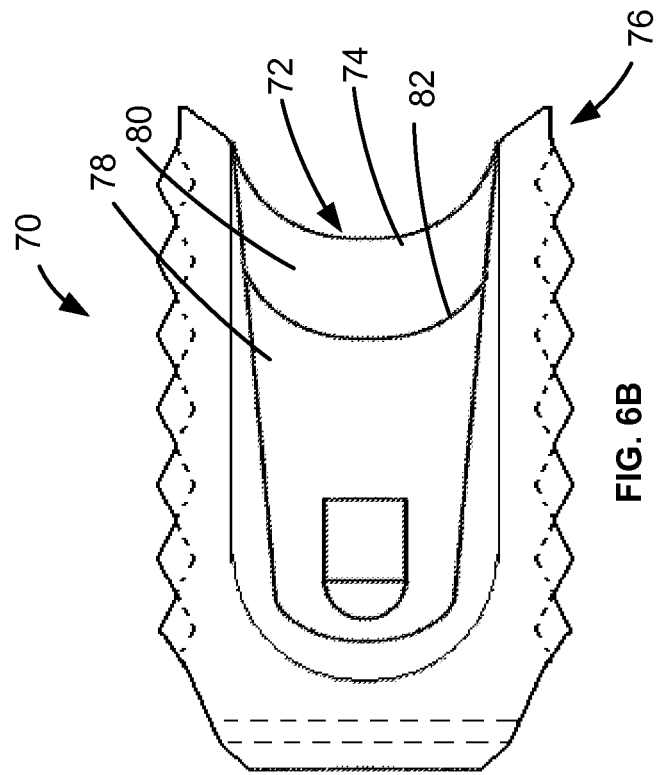
FIG. 6B illustrates a side view of a spacer formed in accordance with an embodiment of the present invention.
Figure 6A:
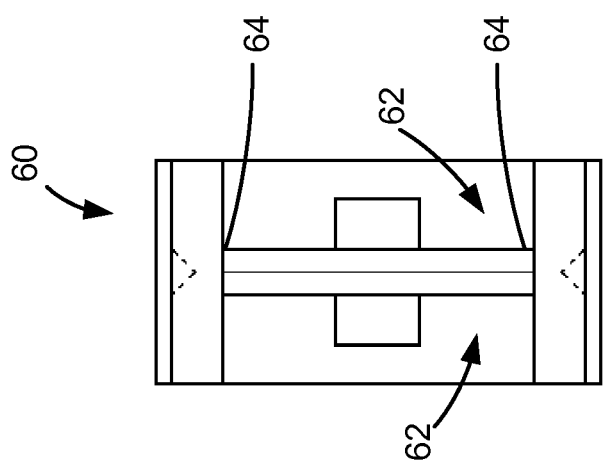
FIG. 6A illustrates an end view of a spacer formed in accordance with an embodiment of the present invention viewed from the proximal end.

FIG. 6A illustrates an end view of a spacer 60 formed in accordance with an embodiment of the present invention, as viewed from the proximal end. The spacer 60 may be similar in many respects to the spacer 10 illustrated in FIGS. 1-4, for example the spacer may include cutouts 62 that form a web. The cutouts 62 of spacer 60 may differ, however, in that they may not have the rounded, or scooped, profile of cutouts 32 of spacer 10. As shown in FIG. 6A, the cutouts 62 have generally perpendicular corners 64. The web formed by cutouts 62 may include one or more surfaces, for example two surfaces located on opposite sides of the web. The surfaces of the web may act to help distribute or disperse bone graft material to either side of the spacer 60 as bone graft material is supplied to the site of interest. Similar to the spacer of FIGS. 1-4, the depth of the cutouts 62 into the sides may increase proximally along at least a portion of the length of the cutout. Put another way, the web may include one or more surfaces that slope inward (toward each other) proximally so that the distance between the sloped surfaces decreases proximally. Thus, the web of the spacer 60 may also be seen as forming a wedge, with the sharper portion of the wedge oriented proximally. Numerous alternative cutout shapes (and by association, web shape shapes and surface shapes) are possible. For example, the slope of the surfaces of the web as it progresses proximally may be linear, curved, or stepped. Further, a series of cutouts may be employed, or the area of the side that is cut into may vary. Further, when viewing the spacer 60 toward the proximal end, the surfaces/cutouts may be substantially straight (from top to bottom), or they may be channeled (for example, like the rounded or scooped style depicted in the spacer of FIGS. 1-4).

Surfaces formed by cutouts (for example, the cutouts 62 of spacer 60 or the cutouts 32 of spacer 10) may be made of the same material as the rest of the spacer, or they may be made of a different material. For example, the surfaces may be made of PEEK (polyether ether ketone), titanium, carbon fiber, bone allograft, or a plurality of materials. Surfaces may be solid in certain embodiments, and, in other embodiments, may include a hollow or perforated portion or portions.

FIG. 6B illustrates a side view of a spacer 70 formed in accordance with an embodiment of the present invention. The spacer 70 may be similar in many respects to the spacers 10 and 60 previously discussed. As seen in the side view illustrated in FIG. 6B, the web 72 of the spacer 70 includes a circular cutout 74 proximate to the proximal end 76. Each side/surface of the web 72 of spacer 70 defines a first sub-surface 78 and a second sub-surface 80. The second sub-surface 80, as seen from the side, is defined by a curved edge 82, which locates the transition from the first sub-surface 78 to the second sub-surface 80. The sub-surfaces 78, 80 may have a slope, for example the sub-surfaces may slope inward toward each other moving proximally. The inward slope of the second sub-surface 80 as it progresses proximally may be greater than the inward slope of the first sub-surface 78. Thus, the web 72 of the spacer 70 may define two differently sloped sub-surfaces as it progresses toward the proximal edge of the web.

As can be seen in FIGS. 5-7, spacers may include a body that is shaped differently than the spacers depicted and described in relation to FIGS. 1-4. For example, referring to FIG. 5B, the spacer 250 may have curved top 254 and bottom 256 and the top and bottom may include more prominent ridges. In another example, referring to FIG. 7, the proximal end of the spacer when viewed from the top may substantially form a point, and the sides of the spacer may be curved smoothly instead of the angular sides depicted in FIGS. 1-4. It should be understood, however, that the descriptions provided herein of implant systems, inserters and the like may apply to many varieties of shapes of spacers, including the spacer shapes of FIGS. 1-7, and other shapes, for example as shown in other figures such as FIG. 8.

FIG. 7 illustrates a side view of a spacer 84 formed in accordance with an embodiment of the present invention. FIG. 7 also illustrates a perspective view of an implant system 83 including an inserter 85 joined to a spacer 84. The inserter 85 includes a shaft 86 and a gripping portion 88. The gripping portion 88 is adapted to grasp and release the spacer 84. The gripping portion 88 includes a first half 90 and a second half 92, which are capable of being biased by a grasping mechanism of the shaft 86. For example, the shaft 86 may include a tapered portion associated with threads on the inside of the shaft that may be turned one way to tighten the gripping portion 88 (that is, bring the two halves together) and turned in the opposite direction to loosen the gripping portion 88 (that is, allow the two halves to move apart from each other).

In the illustrated embodiment, the gripping portion 88 is sized so that it may include a load bearing portion 94 that defines a cross-sectional area corresponding to the cross-sectional area of the spacer 84, such that the load bearing portion 94 contacts the vertebrae during the rotation of the inserter 85 and spacer 84 and thereby takes some of the load encountered as the assembly contacts the vertebrae and distracts the vertebrae. In other embodiments, the gripping portion 88 may define a smaller volume such that it does not contact the vertebrae or take any load during the rotation process.

Each half of the gripping portion 88 of the illustrated inserter 85 includes a feature or features for gripping the spacer 84. In the illustrated embodiment, the spacer 84 includes buttons 87 on each side. For example, a button may extend from a surface of a cutout, or for example the first sub-surface 78. Each opening 93 of the gripping portion 88 includes a graft opening 95 and a slot 96. The slot 96 is sized to cooperate with a feature of the spacer 84 (for example, button 87) to allow the spacer 84 to align with and be retained by the inserter 85. Alternatively, the button 87 can be absent and the slot 96 eliminated to create a solid device holder. The graft opening 95 is sized to allow bone graft material to be supplied via the inside of the shaft 86, to be distributed to either side of the spacer 84, and then to pass through the graft opening 95. As bone graft material accumulates along the sides of the spacer 84 and the gripping portion 88 of the inserter 85, the accumulating bone graft material may make removal of the inserter 85 more difficult. Further, removal of the inserter 85 after bone material has been added may result in the disturbance and/or removal of bone graft material from its desired delivery location. Thus, in certain alternate embodiments, the inserter is disengaged from the spacer before bone graft material is supplied. In such embodiments, the shaft may be solid, and/or the graft opening may be smaller or not present.

As mentioned above, in certain embodiments, the inserter may be removed before addition of bone graft material. In certain embodiments where the inserter is removed before the addition of bone graft material, or where additional bone graft material is desired to be added after the removal of the inserter, a funnel may be used to supply bone graft material to the site of interest around the spacer. Funnels provided by various embodiments of the present invention may provide a variety of shapes, including, for example, circular, oval, or otherwise round, or a polygon shape such as square or rectangular, as well as symmetric or asymmetric. Further, funnels of certain embodiments may have generally constant cross-sectional shapes and areas, or may have different cross-sectional shapes and/or areas at various points along their length. In certain embodiments, a plunger is provided to help push bone graft material through the funnel to the site of interest. The plunger is sized and adapted to be received by the interior of the funnel with a slight clearance to allow the plunger to be moved along the length of the funnel.

Figure 8:
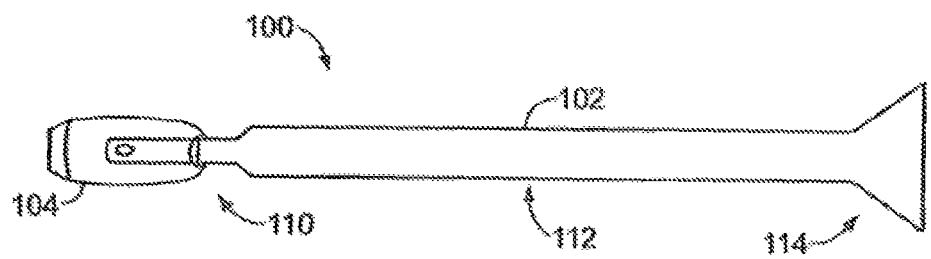
FIG. 8 illustrates a side view of an implant system including a funnel formed in accordance with an embodiment of the present invention.
Figure 9:
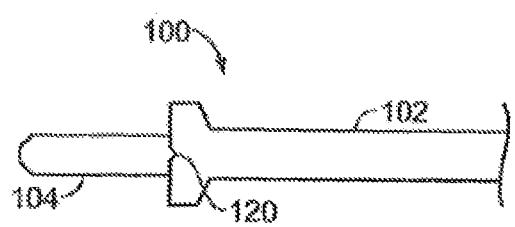
FIG. 9 illustrates a top view of the implant system of FIG. 8.

FIG. 8 illustrates a side view of a spinal implant system 100 including a funnel 102 and a spacer 104 formed in accordance with an embodiment of the present invention, and FIG. 9 illustrates a top view of the system 100. In FIGS. 8-9, the funnel 102 is shown positioned to deliver bone graft material to the spacer 104. In certain embodiments, the overall length of the funnel 102 is about 8 inches. The spacer 104 may be similar in many respects to the spacers discussed above. The funnel 102 includes a distal portion 110, an intermediate portion 112, and a proximal portion 114. The distal portion 110 includes a notch 120 sized and configured to cooperate with the leading edge of the web of the spacer 104 to align the funnel 102 and spacer 104 during delivery of bone graft material. In alternate embodiments, the distal portion may be adapted to cooperate with one or more caps and/or one or more features located on a cap or caps of a spacer to position and align the funnel. In further alternate embodiments, the distal portion of the funnel may be adapted to cooperate with features located on the web as well as the caps of the spacer, or with features located on a body of a spacer.

In the illustrated embodiment, the intermediate portion 112 is a generally circular tube, sized to provide a desired amount of bone graft material to a site of interest. For example, in certain embodiments, the intermediate portion 112 may have an outside diameter of approximately 9 millimeters. The proximal portion 114 is enlarged to provide for easier addition of bone graft material. The distal portion 110 of the illustrated funnel 102 has a substantially oval cross section, with a reduced height and increased width relative to the spacer 104, allowing for more efficient distribution of bone graft material to the sides of the spacer 104. In alternate embodiments, for example, a funnel may have a substantially oval shaped cross section along its entire length. Such a cross-section may be generally equally sized along the length of the funnel, or may, for example, expand to a greater cross-sectional area toward the distal end of the funnel. In certain embodiments, the transition from the smaller cross section to the larger is as short as practicably feasible. Further, in certain embodiments, the funnel includes vents to ease movement of the plunger.

Figure 10:
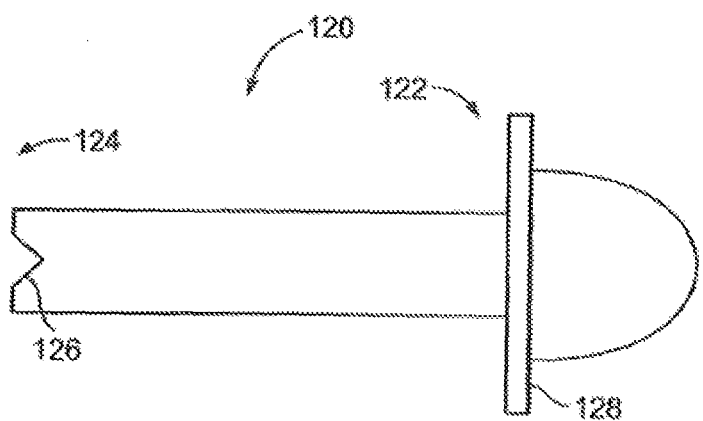
FIG. 10 illustrates a top view of a plunger formed in accordance with an embodiment of the present invention.

FIG. 10 provides a top view of a plunger 120 formed in accordance with an embodiment of the present invention. The plunger 120 illustrated in FIG. 10 is designed to work with a funnel having a generally oval cross-section, and to advance bone graft material distally through the funnel. A variety of sizes of funnel and plunger may be provided to accommodate a variety of sizes required for various patients and procedures. For example, in certain embodiments, generally oval plungers for use with oval funnels may be sized in a range from about 3 millimeters to about 17 millimeters in width and from about 5 millimeters to about 20 millimeters in height. In alternate embodiments, the plunger may take different shapes. For example, a substantially circular plunger could be used with a funnel that is substantially circular along most of its length, and a substantially rectangular plunger could be used with a funnel that is substantially rectangular along its length. The plunger 120 includes a proximal end 122 and a distal end 124, and a notch 126 located proximate to the distal end 124. The notch 126 is sized to cooperate with a corresponding feature on a spacer (similar to the above discussion regarding the funnel). In alternate embodiments, the plunger may not include such a notch. Additionally, the plunger (and/or funnel the plunger is designed to cooperate with) may include a stop or other features designed to prevent the plunger from being inserted too deeply into the funnel. For example, the plunger could include a handle 128 or tab (not shown) at its proximal end extending out from the body of the plunger to prevent the proximal end of the plunger from extending past a selected point such as the proximal end of the funnel.

Figure 11:
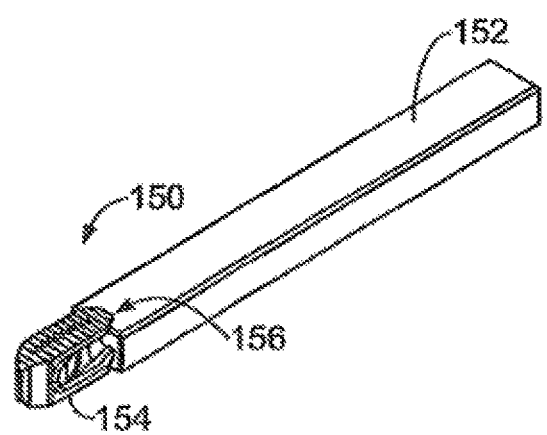
FIG. 11 illustrates a perspective view of an implant system including a rectangular, symmetric funnel formed in accordance with an embodiment of the present invention.
Figure 12:
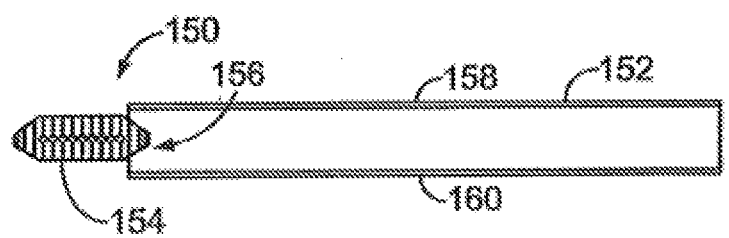
FIG. 12 illustrates a top view of the implant system of FIG. 11.

FIG. 11 illustrates a perspective view of a spinal implant system 150 including a funnel 152 and a spacer 154, and FIG. 12 illustrates a top view of the spinal implant system 150. As can best be seen in FIG. 12, the funnel 152 is symmetric about a vertical plane through the center of the spacer 154 when the spacer 154 and funnel 152 are positioned in place during a procedure to provide bone graft material to a site of interest. The funnel 152 illustrated in FIGS. 11 and 12 is generally rectangular and is wider than it is high, allowing for greater distribution of bone graft material around the sides of the spacer 154 than to the top or bottom of the spacer 154. For example, in certain embodiments, the funnel is formed from a rectangular tube having a height of about 7 millimeters, a width of about 11 millimeters, and a wall thickness of about 0.5 millimeters. In other embodiments, different sizes and shapes, such as generally circular or oval funnels, may be used. The illustrated funnel 152 includes an alignment feature 156 configured to cooperate with a feature of the spacer 154 to help properly align the funnel 152 with the spacer 154 during delivery of bone graft material. For example, in the illustrated embodiment, the alignment feature 156 comprises a notch cut through both the top and bottom walls of the funnel 152 that accepts a portion of the caps of the spacer 154. In alternate embodiments, an alignment feature may be configured to accept the web of a spacer, the web and the caps of a spacer, or a different portion of a spacer. The width of the funnel 152 is such that its sides 158, 160 are located laterally far enough away from the alignment feature to allow bone graft material to flow to both sides of the spacer 152.

Figure 13:
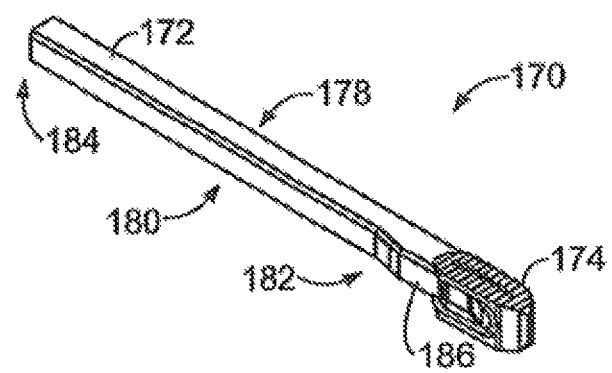
FIG. 13 illustrates a perspective view of an implant system including a rectangular, asymmetric funnel formed in accordance with an embodiment of the present invention.
Figure 14:
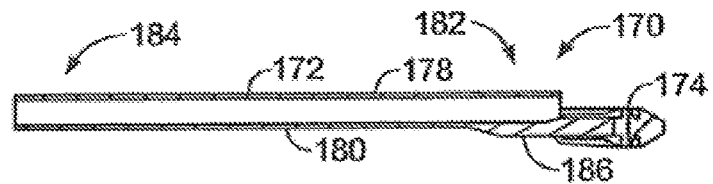
FIG. 14 illustrates a top view of the implant system of FIG. 13.

FIG. 13 illustrates a perspective view of a spinal implant system 170 including a funnel 172 and a spacer 174, and FIG. 14 illustrates a top sectional view of the spinal implant system 170. The funnel 172 includes a distal end 182 and a proximal end 184. As can best be seen in FIG. 14, the funnel 172 is asymmetric about a vertical plane through the center of the spacer 174 when the spacer 174 and funnel 172 are positioned in place during a procedure to provide bone graft material to a site of interest. The funnel 172 illustrated in FIGS. 12 and 14 is generally square shaped along most of its length, with an offset 186 toward its distal end 182. For example, the funnel 172 may generally include a generally square length of tubing with an additional amount of solid material added to form the offset 186. The two pieces may, for example, be soldered together and then heat treated to make the funnel 172. In certain embodiments, the tubing portion of the funnel 172 may be about 5.5 millimeters by 5.5 millimeters with a wall thickness of 0.5 millimeters. The illustrated funnel 172 is configured to cooperate with the web of the spacer 174 to align the funnel 172 and spacer 154. In alternate embodiments, an alignment feature may be configured to accept the caps of a spacer, the web and the caps of a spacer, or a different portion of a spacer. For instance, a funnel otherwise generally similar to funnel 172 may be configured to cooperate with features on the cap of a spacer to align the spacer and funnel. For example, in certain embodiments, a funnel designed to engage the cap of a spacer similarly sized to spacer 174 may have a height of about 7.0 millimeters, a width of about 5.50 millimeters, and a wall thickness of 0.5 millimeters along most of its length. The illustrated funnel 172 includes an alignment feature 176 configured to cooperate with a feature of the spacer 174 to help properly align the funnel 172 with the spacer 174 during delivery of bone graft material. For example, in the illustrated embodiment, the alignment feature 176 comprises a notch cut through of the height of the funnel 172 and through a portion of the offset 186 that accepts the leading edge of the web of the spacer 174. Thus, the alignment feature 176 is off-center of the funnel, allowing first side 178 of the funnel to protrude laterally further away from the center of the spacer 154 than second side 180 protrudes. The width of the funnel 172 is such that first side 178 is located laterally far enough away from the corresponding side of the spacer to allow bone graft material to flow to its side of the spacer 174, but second side 180 is located laterally closer to the alignment feature such that either a smaller amount of bone graft material, or no bone graft material, is allowed to flow to its side of the spacer 174. To use such an asymmetric funnel, the funnel would first be positioned to provide bone graft material to one side of the spacer. Once a sufficient amount of bone graft material was provided to one side of the spacer, the funnel would be removed, rotated 180 degrees, and re-positioned to provide bone graft material to the other side of the spacer. Use of such an asymmetric funnel allows for a smaller overall cross-sectional area of the funnel, thereby aiding to make the required procedure less invasive. Further, use of such an asymmetric funnel makes it easier to provide different quantities of bone graft material to different sides of a spacer.

Figure 15:
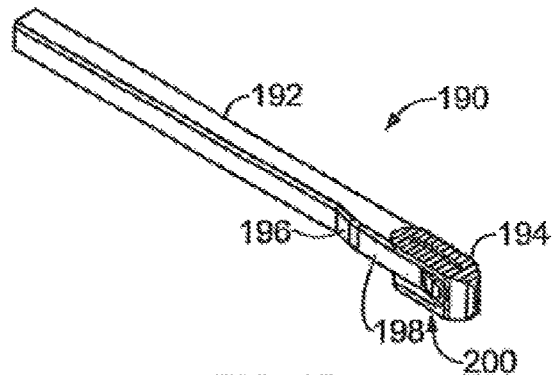
FIG. 15 illustrates a perspective view of an implant system including a funnel formed in accordance with an embodiment of the present invention.

FIG. 15 illustrates a perspective view of a spinal implant system 190 including a funnel 192 and a spacer 194. The funnel 192 may be generally similar to funnel 172, discussed above, in many respects. However, funnel 192 further includes an arm 198 extending from an offset 196. Toward the distal end of the arm 198, the arm 198 includes a securement feature 200 configured to cooperate with a feature of the spacer 194 to more securely connect the funnel 192 to the spacer 194. For example, the securement feature 200 may comprise a pin adapted to be accepted by a hole in the spacer 194. Other arrangements are possible. For example, the securement feature 200 may be a slot similar to the above describe slot of an inserter that accepts a button of the spacer. As a further example, the securement feature may be a sloped or otherwise shaped surface that corresponds to a portion of the surface of the cutout of the spacer that is accepted by the cutout in a generally snug fit.

Figure 16:
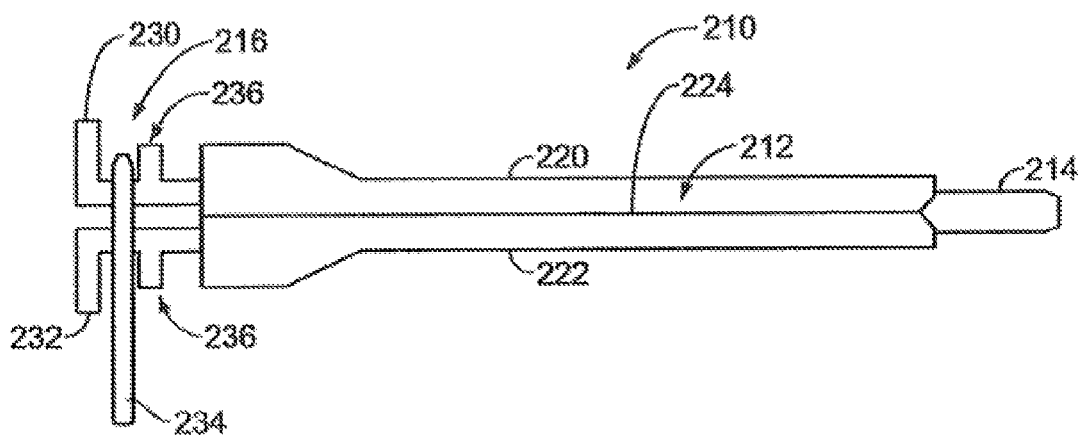
FIG. 16 illustrates an overhead view of a spinal implant system including a funnel, a spacer, and a double-barreled plunger formed in accordance with an embodiment of the present invention.
Figure 17:
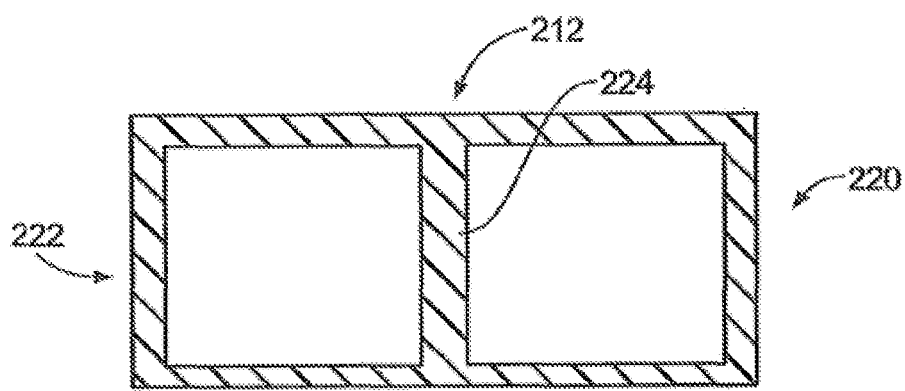
FIG. 17 illustrates a sectional view through the funnel of FIG. 16.

FIG. 16 illustrates an overhead view of a spinal implant system 210 including a funnel 212, a spacer 214, and a double-barreled plunger 216, and FIG. 17 illustrates a sectional view of the funnel 212. While the spinal implant system 210 is similar in many respects to the above described embodiments, the spinal implant system 210 further allows choosing between simultaneous and independent delivery of bone graft material to either side of the spacer 214.

The funnel 212 includes a length that is generally rectangular, and includes a first portion 220 and a second portion 222 separated by a wall 224 that runs along the length of the funnel 212. In alternate embodiments, the wall may not run along the entire length of the funnel. In the illustrated embodiment, the funnel 212 is substantially rectangular, with a width greater than its height. In alternate embodiments, different shapes may be used, such as, for example, generally oval. The funnel 212 is sized to provide a desired amount of bone graft material to either side of the spacer 214, while still maintaining a desired size to reduce the invasiveness of its use.

The double-barreled plunger 216 includes a first plunger 230, a second plunger 232, and a handle 234. The first plunger 230 and second plunger 232 are generally similar, and configured to be accepted by a portion of the funnel 212 to advance bone graft material down that half of the funnel 212. Each plunger 230, 232 includes a grasping portion 236 proximate to its proximal end. In the illustrated embodiment, the grasping portion 236 is configured to perform two functions. First, the grasping portion 236 may be handled by a practitioner to advance one plunger 230, 232 at a time through the funnel 212, thereby advancing bone graft material only along one half of the funnel and to only one side of the spacer 214, or allowing the plungers 230, 232 to be advanced independently of each other at different rates and/or for different lengths of advancement. Second, the grasping portions 236 may be joined to the handle 234 to advance both plungers 230, 232 simultaneously. The handle 234 includes features that cooperate with features of the grasping portions 236 to join the first and second plungers 230, 232 to the handle 234. For example, the handle 234 may include slots that accept portions of the grasping portions 236. Thus, the spinal implant system 210 allows for either independent or simultaneous distribution of bone graft material to either side of the spacer 214, thereby allowing greater control of the volume and location of bone graft material distributed.

For example, both portions of the funnel 212 may be filled with bone graft material, both plungers depressed, and a generally equal amount of bone graft material distributed to each side of the spacer 214. However, if one side requires more bone graft material than first distributed, but the other side does not, then additional bone graft material may be added only to the desired portion of the plunger. As another example, if the plungers are initially depressed, and it is discovered that along the length of their travel that one, but only one side, has all the bone graft material desired, then the handle 234 may be decoupled from the plungers 230, 232, and only the plunger on the side still requiring bone graft material may be advanced.

Figure 18:
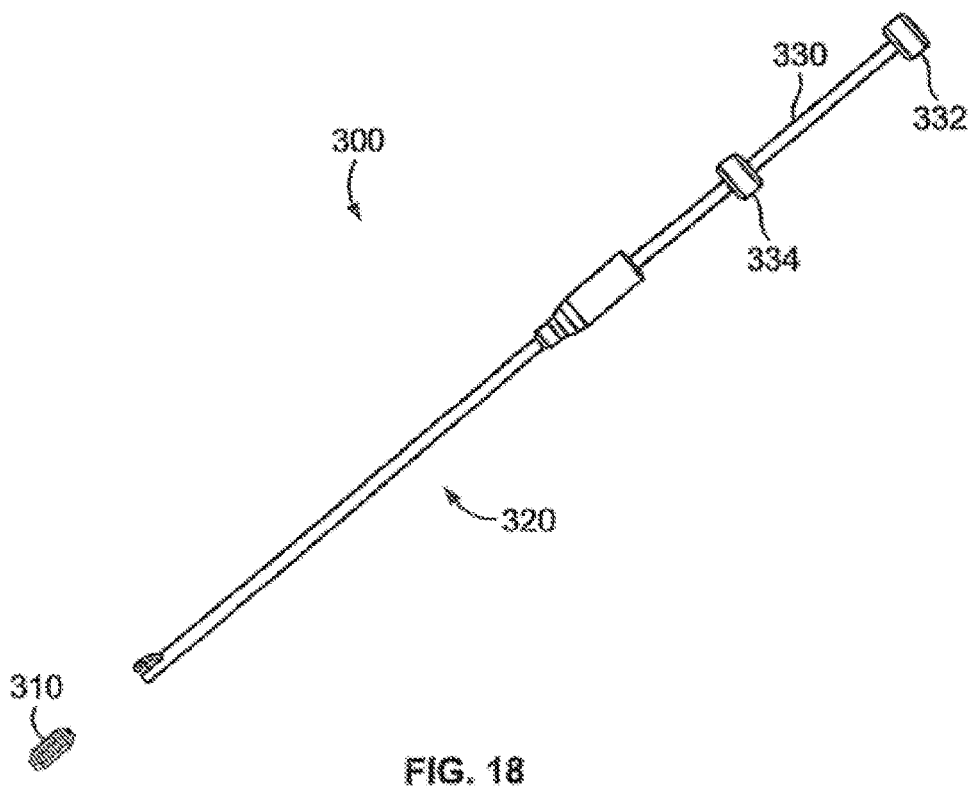
FIG. 18 illustrates a perspective view of a spinal implant system including a funnel, a spacer, and a tamping rod.

FIG. 18 illustrates a perspective view of a spinal implant system 300 formed in accordance with an embodiment of the present invention. The spinal implant system includes a spacer 310, a funnel 320, and a tamping rod 330. The spacer 310 may be similar in many respects to the spacers discussed above. The illustrated funnel 320 is asymmetric, similar to funnel 172, for example. Funnel 320, however, is generally circular in cross-section along most of its length. Further, the funnel 320, toward its proximal end, includes a mouth having a larger diameter to ease insertion of bone graft material. The tamping rod 330 is a type of plunger. The tamping rod 330 includes a handle 332 and a stop 334. The handle 332 is a generally circular shaped feature, located at the proximal end of the tamping rod 330, and configured to provide a convenient location for grasping of the tamping rod 330 by a practitioner. The stop 334 is a generally circularly shaped feature, located at a length along the tamping rod 330 to prevent the tamping rod 330 from being urged too far down the funnel 320, where the tamping rod could otherwise potentially disturb aspects of a patient's anatomy and/or the placement of the spacer 310 between the patient's vertebrae. In the illustrated embodiment, the stop 334 has a diameter sufficient large to prevent it from advancing beyond the proximal edge of the enlarged bell mouth of the funnel 320.

To use a spinal implant system in accordance with an embodiment of the present invention, the following steps may be performed. First, an incision is made to access the site of interest. Next, a pocket for placement of a spacer is prepared, for example, by scraping surfaces of the vertebrae to be fixed. Next, the correct size of spacer is selected. The spacer may be joined to an inserter, and advanced to the site of interest in its horizontal orientation. Then, the inserter (and spacer with it) is rotated to position the vertebrae as desired. The inserter is then removed and a funnel positioned. For example, if during the creation of the pocket the practitioner observes that one side is likely to require a different volume of bone graft material than the other, an asymmetric funnel may be selected, or alternatively, a plunger with a double-barreled funnel selected. The bone graft material is then added as desired.

Figure 19:
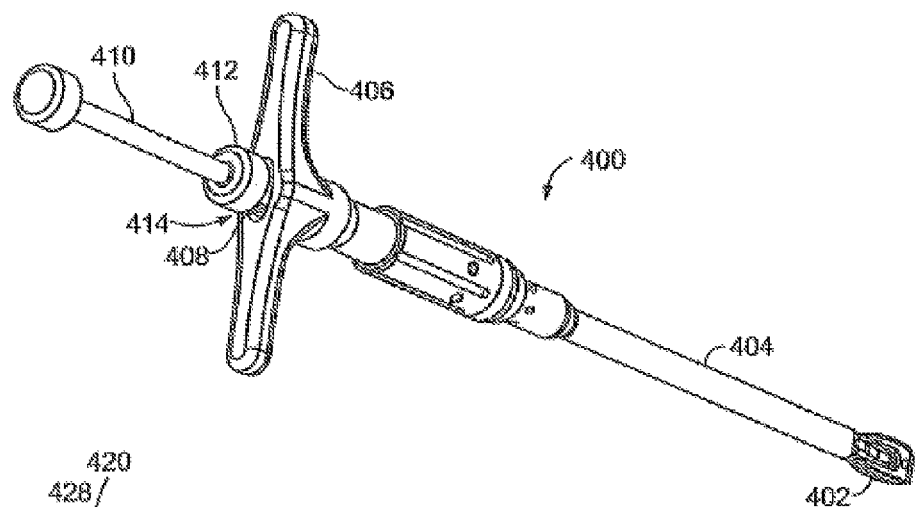
FIG. 19 illustrates a perspective view of a spinal implant system formed in accordance with an embodiment of the present invention including a funnel, a spacer, a bone graft cartridge, and a tamping rod.

FIG. 19 illustrates a perspective view of a spinal implant system 400 formed in accordance with an embodiment of the present invention. The spinal implant system 400 includes a spacer 402, a funnel 404, a bone graft cartridge 408, and a tamping rod 410. The spacer 402, for example, may be formed substantially similarly to above described spacers. In different embodiments, different types of spacers, such as, for example, hollow spacers, may be used. In the illustrated embodiment, the tamping rod 410 includes a stop 412, positioned to prevent the tamping rod 410 from advancing further than necessary to help deliver bone graft material. The funnel 404 provides a conduit through which bone graft material may be advanced to the site of interest, and includes a handle 406. In the illustrated embodiment, the funnel 404 also has features for grasping or otherwise engaging the spacer 402, and the funnel 404 may also be considered an inserter. In alternate embodiments, separate inserter and funnels may be employed. The handle 406 includes an opening sized and configured to accept the bone graft cartridge 408.

Certain embodiments of the present invention, such as the embodiments depicted in FIGS. 19-22, helps provide further improved control of bone graft material as it is introduced into a patient. When graft material is introduced freely or arbitrarily into a funnel or operative site, for example, the material may bind up, preventing insertion of additional material, or making such insertion difficult. Further, the amount of material added may be difficult to control. By using bone graft material, for example pre-measured and/or pre-formed as a unit, such as bone graft pellets, capsules, or bullets, either alone or in connection with a bone graft container such as a cartridge, embodiments of the present invention provide greater control over the addition of bone graft material, including greater control of the volume introduced, to a site of interest.

Figures 20, 21:
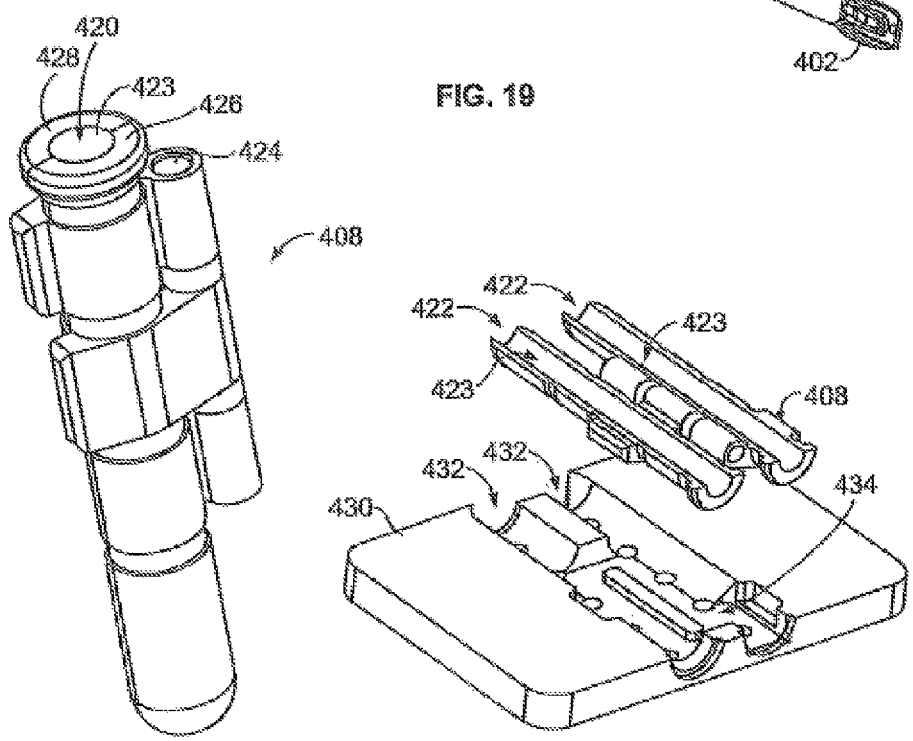
FIG. 20 illustrates a perspective view of a bone graft cartridge formed in accordance with an embodiment of the present invention.
FIG. 21 illustrates a perspective view of a bone graft cartridge and cartridge loader formed in accordance with an embodiment of the present invention.

For example, FIG. 20 illustrates a perspective view of the bone graft cartridge 408 configured for use with the spinal implant system 400. FIG. 21 illustrates a perspective view of the bone graft cartridge 408 with a cartridge loader 430, and FIG. 22 illustrates the bone graft cartridge 408 positioned inside the cartridge loader 430.

The bone graft cartridge 408 is an example of a bone graft container, and includes a first opening 420 and a second opening 422. The first opening 420 is located proximally, and the second opening 422 is oriented distally (the second opening 422 can be understood more clearly with reference to FIG. 21). A chamber 423 for holding bone graft material, for example a bone graft pellet, is defined between the first opening 420 and the second opening 422. The first opening 420 allows the tamping rod 410 to push bone graft material held within the bone graft cartridge 408, and the second opening 422 allows the tamping rod 410 and bone graft material to be advanced into the funnel 404 and toward the site of interest. In the illustrated embodiment, the bone graft cartridge 408 has a substantially constant inner diameter between the first opening 420 and the second opening 422, and the tamping rod 410 has a diameter sized to fit through these openings with a slight clearance. Further, the funnel 404 includes an inner diameter sized substantially the same as the bone graft cartridge's inner diameter, so that the tamping rod 410 may push the bone graft material down the funnel 404 as well.

The bone graft cartridge 408 includes a hinge 424 joining a first half 426 and a second half 428. In the illustrated embodiment, the bone graft cartridge 408 is hinged to allow it to be folded open to accept bone graft material, and to be closed to be inserted into the funnel. In other embodiments, the bone graft cartridge may be configured differently. As one example, the bone graft cartridge may be composed of separate halves, or clamshells, that can be joined together and separated. As another example, the cartridge could be solid and have a pre-formed bone graft pellet inserted into one end. In the illustrated embodiment, which includes a hinged bone graft cartridge 408, the opening 414 of the handle 406 of the funnel 404 is sized and shaped to accommodate the hinge when the bone graft cartridge 408 is inserted into the opening 414. Further, the opening and the bone graft cartridge may have cooperating surfaces, such as a tapered surface proximate the distal end of the cartridge and opening, to provide a mechanical stop and prevent the cartridge from being pushed deeper into the opening when the bone graft material is pressed our of the cartridge by the tamping rod.

Figure 22:
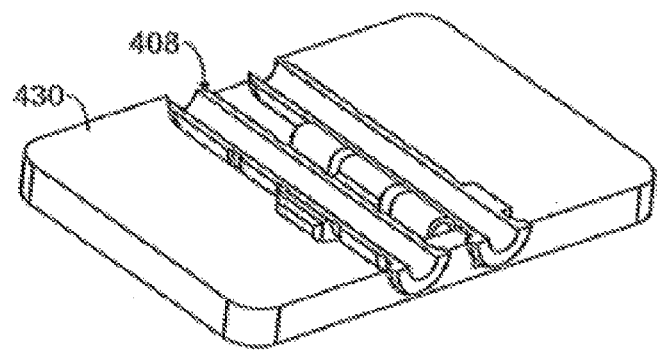
FIG. 22 illustrates the bone graft cartridge of FIG. 21 positioned inside the cartridge loader.

FIGS. 21 and 22 illustrate a cartridge loader 430 for use with the bone graft cartridge 408. As seen in FIG. 22, the cartridge loader 430 includes cartridge slots 432 and a hinge slot 434. The cartridge slots 432 are sized to accept one of the halves of the bone graft cartridge 408, while the hinge slot 424 is interposed between the cartridge slots 432 and is sized to accept the hinge 424 of the bone graft cartridge 408.

With the bone graft cartridge 408 in place in the cartridge loader 430, bone graft material can be added to the bone craft cartridge 408, and may also be formed into a bone graft pellet. For example, in some embodiments, the cartridge loader 430 may be made of a foam or other flexible material, and once bone graft material has been added in loose form to both halves of the bone graft cartridge 408, the cartridge loader 430 may be folded (with the cartridge still inside) to join the two halves of the bone graft cartridge 408. Excess graft material, if any, may be forced out of the openings at either end of the bone graft cartridge 408. In alternate embodiments, a bone graft cartridge may be loaded with bone graft material without the use of a cartridge loader. For example, in certain embodiments, a bone graft cartridge could be held by hand and folded without the use of the loader. As another example, in certain embodiments, a pre-formed bone graft pellet may be inserted into the bone graft cartridge. As another example, in certain embodiments, a bone graft cartridge may not be used, and instead a pre-formed bone graft pellet placed directly into an opening in the funnel. In such an embodiment, for example, a cylindrical bone graft pellet having a diameter of less than about 5 millimeters may be inserted directly into an opening in a funnel/inserter that is sized to accept the pellet, and advanced through the opening toward the site of interest with a tamping rod.

Further still, the use of pre-formed bone pellets and/or pre-loaded bone graft cartridges, or other unit of bone graft material of pre-determined size and/or shape, facilitates more precise control of the volume of bone graft material added, and, when used with, for example, a tamping rod, can help minimize waste or residual material left in a funnel. For example, for many patients and procedures, graft material in a range of between about 2 cubic centimeters and about 7 cubic centimeters will be used. Pre-formed pellets of about 1 cubic centimeter, for example, may be used. Such pellets may be added to the site of interest one at a time until the desired volume is achieved. Further, depending on the volume to be filled, after several pellets have been added, only part of a pellet may be required. In such a circumstance, a practitioner may load a full pellet into the funnel, but only partially advance the tamping rod, resulting in only a portion of the pellet being introduced to the site of interest. In alternate embodiments, multiple sizes of pellets may be provided, with a smaller pellet or pellets (or, alternatively, broken off portions of larger pellets) being utilized as the site of interest fills. The pellets preferably are formed with a sufficient consistency to generally maintain their shape when handled and when advanced through the funnel, but are also easily broken up and distributed around the spacer in the site of interest. For example, the pellet may generally maintain its shape while being advanced down a funnel, but then be readily separated and distributed to either side of the spacer, for example by a wedge shape at the spacer's proximal end, and then conform to the desired shape of the volume of the site of interest. In embodiments that utilize a cartridge, once the bone graft material has been added to the site of interest, the tamping rod may be be removed from the funnel, and the now substantially empty cartridge then removed. Alternatively, if it is known that several units of bone-graft material may be required, a first pellet may be advanced partially down the funnel, the tamping rod withdrawn, and the cartridge removed. A subsequent pellet or pellets may also then be similarly introduced into the funnel, with the tamping rod eventually used to advance several pellets from a location partially down the length of the funnel and toward the site of interest.

Figure 23:
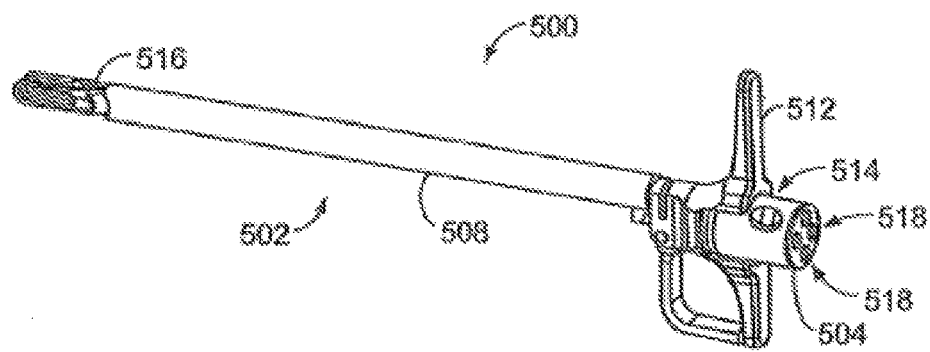
FIG. 23 illustrates a perspective view of a spinal implant system formed in accordance with an embodiment of the present invention including a funnel, a spacer, and a plurality of bone graft cartridges.
Figure 24:
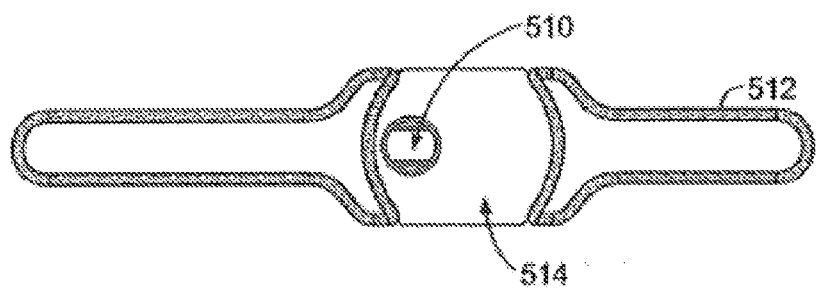
FIG. 24 illustrates a plan view of the funnel of the spinal implant system of FIG. 23.

FIG. 23 illustrates a perspective view of a spinal implant system 500 formed in accordance with an embodiment of the present invention, and FIG. 24 illustrates a plan view of the funnel of the spinal implant system of FIG. 23 (with the carousel removed). The spinal implant system 500 includes a funnel 502 and a carousel 504. In the illustrated embodiment, the funnel 502 includes a gripping mechanism for grasping a spacer and also acts as an inserter. Again, in alternate embodiments, separate funnels and inserters may be employed.

The funnel 502 provides a conduit through which bone graft material may be advanced to a site of interest. The funnel 502 includes a body 508, a graft passageway 510, a handle 512, a carousel opening 514, and a gripper 516. The system 500 may also include a tamping rod (not shown) for advancing bone graft material down the funnel 502. The graft passageway 510 passes through the body 508 and provides a conduit for bone graft material. The graft passageway, for example, may have a diameter of about 5 millimeters. In the illustrated embodiment, the gripper 516 is positioned at a distal end of the funnel 502 and is configured to grasp a spacer (not shown) to permit, for example, insertion and rotation of the spacer. For example, the gripper 516 may include slots that accept projections of a spacer. Further, the slots may be sized to allow room for graft material to pass out of the funnel and around the spacer. The handle 512 is sized and configured to allow a practitioner to grasp and manipulate the funnel 502. In the illustrated embodiment, the handle 512 includes surfaces on either side of the carousel 504 to provide for convenient handling, loading, and rotation of the system 500 including the carousel 504.

The carousel 504 is accepted by the carousel opening 514. The carousel 504 includes a plurality of graft openings 518 arranged in a generally circular fashion disposed about the carousel 504. The graft openings 518 as arranged in the illustrated embodiment are an example of multiple chambers configured to accept pre-formed bone graft units. In certain embodiments, the chambers loose bone graft material or bone graft material that has not been pre-formed may be introduced into the graft openings or chambers. The carousel 504 may be snappably received by the carousel opening 514 and held snugly enough to be maintained in place, but loosely enough to allow for rotation. As best seen in FIG. 24, the center of the graft passageway 510 is offset from the center of the carousel opening 514. The graft passageway 510 is located to allow the graft openings 518 to align with the graft passageway, one at a time, as the carousel 504 is rotated. Further, the carousel 504 and/or handle 512 and/or carousel opening 514 may include detents and/or other cooperating surfaces, and/or visual indicators to assist in the proper alignment of a graft opening 518 with the graft passageway 510.

To use the system 500 to insert bone graft material into a site of interest, the carousel 504 is first loaded with a desired number of bone graft pellets or cartridges. In the illustrated embodiments, a carousel 504 with four graft openings 518 is illustrated. In other embodiments, carousels with more or fewer graft openings may be used. As discussed elsewhere, bone pellets or other bone graft material may be inserted directly into the carousel graft openings, or, as another example, cartridges, each containing a pellet or other bone graft material, may be inserted into the graft openings. Cartridges provide for easier handling outside of the carousel, and may also provide a more positive stop when the graft material is inserted into a graft opening to help prevent over-insertion of a pellet into a graft opening that may result in premature deformation of the pellet, while the use of pellets without cartridges reduces the number of parts required and removes the need for removing cartridges from the carousel once the pellets are advanced into the funnel and/or the site of interest. Once a desired number of graft openings 518 are filled (based, for example, on the volume of bone graft material required for the procedure), the carousel 504 is inserted into the carousel opening 514 of the funnel 502, and one of the graft openings 518 aligned with the passageway 510. In alternate embodiments, the graft material may be placed in the carousel with the carousel already in place in the funnel. Such a carousel may be easily removable from the funnel or, alternatively, may be more permanently secured to the funnel. The bone graft material from the graft opening 518 aligned with the passageway 510 may then be advanced into the passageway 510 and toward the site of interest, for example, with the use of a tamping rod. If more bone graft material is desired to be added to the funnel and/or the site of interest, the carousel 504 may be rotated so that a graft opening 518 containing bone graft material is aligned with the passageway 510, and the bone graft material pre-loaded in that particular graft opening 518 then advanced into the passageway 510 and toward the site of interest. This process may be repeated until a sufficient amount of bone graft material has been added, or until the carousel is emptied. If more material is required, more pellets and/or cartridges, for example, may be added to the carousel. (In embodiments utilizing cartridges, the empty cartridges can be removed from the carousel and replaced with full cartridges.)

The carousel provides an example of a multiple unit graft material loading device. Put another way, the carousel allows the use of a plurality of pre-measured bone graft material units to be loaded into the funnel. The use of such pre-measured bone graft material allows a practitioner better control over the volume of bone graft material added, and/or allows for quicker procedures and/or reduced effort by reducing the need to deal with any clogging in the funnel, and/or the need to handle loose bone graft material, and/or other impediments to efficient procedures. The use of a plurality of such pre-measured bone graft units allows for further convenience and efficiency. Other multiple unit graft material loading devices than carousels may also be employed. For example, in some embodiments, a clip or magazine holding bone graft units in a generally linear fashion may be used. The clip may, for example, be slidably advanced so that the individual bone graft units become aligned with a funnel opening sequentially. Or, as another example, the clip may be stationary, with the bone graft units advanced through the clip as preceding bone graft units are advanced into the funnel, by, for example, a spring mechanism.

As indicated previously, the bone graft material units may take the form of, for example, pre-formed pellets, or, as another example, bone graft material packed into a cartridge. The bone graft material, when added to a cartridge, may be added as a pre-formed pellet to the cartridge, or, as another example, may be added loosely to one or both halves of a cartridge and then formed to take the shape of the interior of the cartridge when the cartridge halves are joined.

Figure 25:
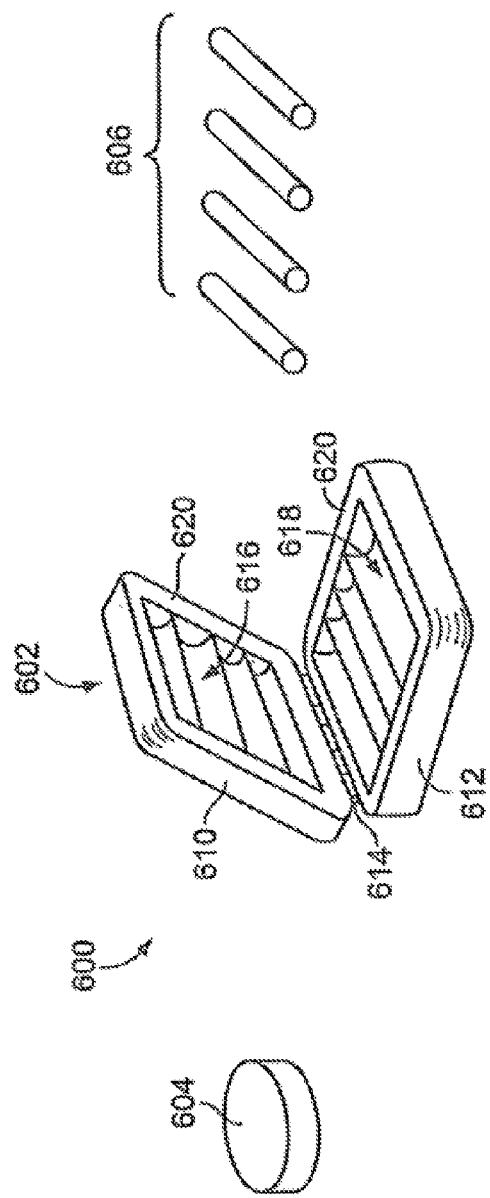
FIG. 25 illustrates a perspective view of a graft pellet press formed in accordance with an embodiment of the present invention.

FIG. 25 illustrates a perspective view of a graft pellet press system 600 formed in accordance with an embodiment of the present invention. The graft pellet press system 600 includes a graft pellet press 602 that forms graft pellets 606 from a graft puck 604. The graft pellets 606 may be used, for example, with systems similar to those discussed above.

In the illustrated embodiment, the graft pellet press 602 includes 4 slots, each sized and configured to produce a pellet 606 that has a volume of about 1 cubic centimeter. Thus, a bone puck having a volume of about 4 cubic centimeters may be used. In alternate embodiments, the size of the pellets and/or the total number of slots and resulting pellets may be different. Further, different size slots may be used in the same device to produce differently sized pellets. In other embodiments, bone graft material may be introduced freely into the graft pellet press instead of being provided by a pre-formed puck. Use of a puck or other pre-measured form provides for convenient handling and also reduces the potential for waste or unused material, as well as the potential for under-sized pellets resulting from using too little bone graft material, by providing a known volume of bone graft material to the graft pellet press.

The graft pellet press 602 includes a top 610 and a bottom 612 joined by a hinge 614. In alternate embodiments, for example, the top and bottom may be separate halves that are brought together, and the top and bottom may include alignment and/or mounting features such as pins and pinholes to help align the top and bottom and secure the top and bottom together. The top 610 defines slots 616 and the bottom 612 defines slots 618, with the slots 616 from the top 610 cooperating with the slots 618 from the bottom 612 to form generally cylindrical shaped volumes for forming the pellets 606 when the top 610 and bottom 612 are brought together. The edges of the slots from the top and bottom need not necessarily meet each other when the top 610 and bottom 612 are brought together, as leaving a small gap between the resulting volumes will allow graft material to flow more freely between slots, allowing for more uniform sized pellets. The slots are surrounded by walls 620. Configuring the walls 620 to meet when the top 610 and bottom 612 are brought together, but allowing a small gap between edges of the volumes formed by the slots 616 and 618, allows graft material to flow between the volumes formed by the slots without escaping from the sides of the device, further improving uniformity of pellet size and reducing potentially wasted graft material.

In the illustrated embodiment, the graft pellets 606 are generally cylindrical and have a volume of about 1 cubic centimeter each. In alternate embodiments, different shapes and/or sizes of pellets may be formed by using differently shaped and/or sized slots in the graft pellet press. As discussed above as well as below, once formed, the pellets may be inserted directly into a funnel or inserter apparatus, or, alternatively, may be placed in a cartridge which is then inserted into the funnel or inserter apparatus. To form the graft pellets 606, the graft puck 604 is placed in one half of the graft pellet press 602, with the graft pellet press 602 in an open position (that is, with the top 610 and bottom 612 not joined). At this time, the puck may be broken up and/or spread or otherwise distributed more evenly to ease the formation of generally evenly sized pellets. Then, the top 610 and bottom 612 of the graft pellet press 602 are brought together to a closed position, forcing graft material into the volumes formed by the slots 616 and 618. Once the graft pellets 606 are formed, the top 610 and bottom 612 are brought apart, and the graft pellets 606 removed from the graft pellet press 602.

Figure 26:
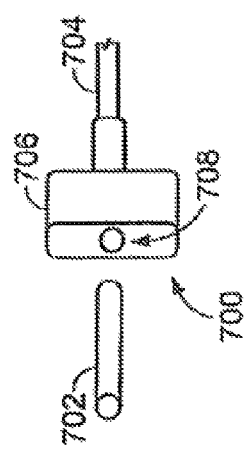
FIG. 26 illustrates a perspective view of a system formed in accordance with an embodiment of the present invention that utilizes pellets that are inserted directly into an inserter.

FIG. 26 illustrates a perspective view of a system 700 that utilizes pellets 702 that are inserted directly into an inserter 704. The inserter 704 includes a handle 706 and an opening 708. The opening 708 is sized to accept a pre-formed pellet 702, and provides an entrance to a conduit that passes to the site of interest through the body of the inserter 704. The pellet 702, for example, may be pre-formed by a device similar to those discussed above. The inserter 704 also includes a gripper (not shown) for handling a spacer (not shown). In alternate embodiments, separate inserters and funnels may be used, with the inserter used to position the spacer and then removed, and then the funnel positioned to deliver bone graft material to the site of interest. In such embodiments, the inserter need not provide a conduit, and the pellet (or pellets) or other bone graft material would be inserted into the funnel instead. The gripper and spacer may, for example, be substantially to similar to grippers and spacers discussed above. In the illustrated system 700, the system is designed to accept one pellet 702 at a time. If it is known ahead of time that more than one pellet may be used, more than one pellet may be advanced into the opening and into the inserter so that several are in a conduit of the inserter at once and advanced as a group by a tamping rod to the site of interest, where the bone graft material separates from its pellet form and is distributed around a spacer. In alternate embodiments, for example, pellets could be inserted into a carousel or similar device. The pellet may, for example, have a volume of about 1 cubic centimeter and a diameter of about slightly less than 5 millimeters, and the opening may have a diameter of about 5 millimeters, allowing the pellet to fight right into the opening of the inserter. In alternate embodiments, larger or smaller sizes of diameter and/or volume may be used.

Figure 27:
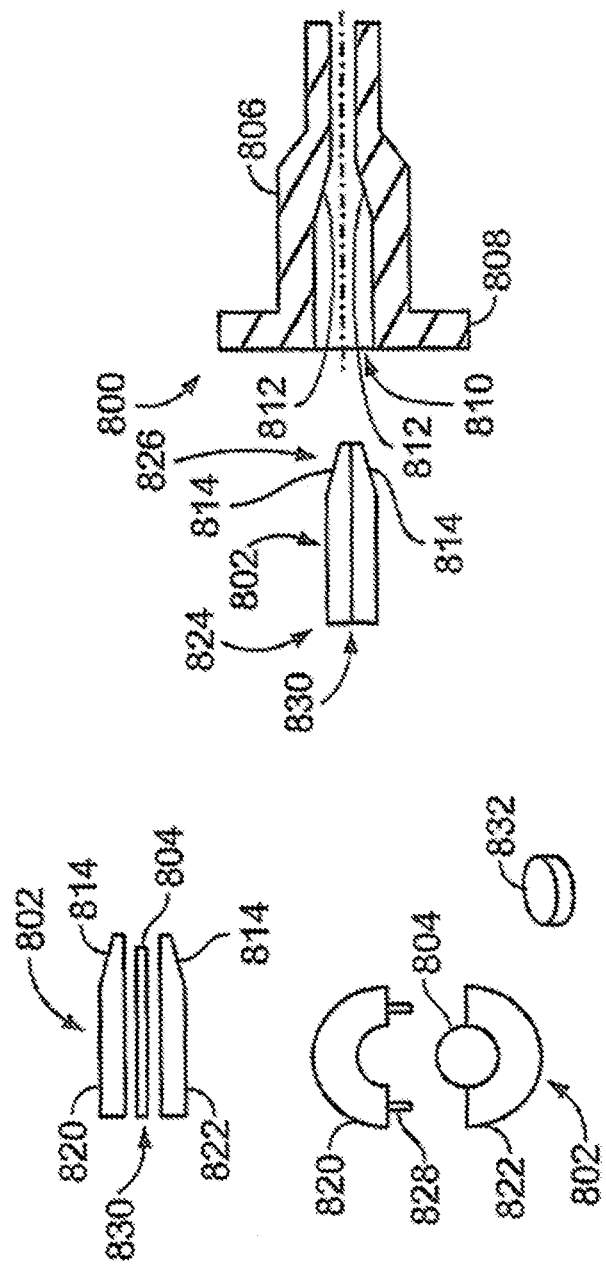
FIG. 27 illustrates a side sectional view of a system formed in accordance with an embodiment of the present invention that utilizes a cartridge to insert a bone graft material into an inserter.

FIG. 27 illustrates a side sectional view of a system 800 that utilizes a cartridge 802 to insert a bone graft pellet 804 into an inserter 806. The inserter 806 includes a handle 808 and an opening 810. The opening 810 is sized to accept the cartridge 802, and includes a forward sloped surface 812 that cooperates with a corresponding sloped surface 814 on the cartridge 802 to provide a mechanical stop to prevent the cartridge 802 from being pressed too deeply into the opening 810. The opening 810 provides an entrance to a conduit that passes to the site of interest through the body of the inserter 806.

The cartridge 802 includes a top half 820 and a bottom half 822, as well as a proximal end 824 and a distal end 826. In FIG. 27, one cartridge is shown from an end view with the halves separated, and one cartridge is shown from a side view with the halves shown joined. The cartridge 802 includes pins 828 in one half that are accepted by holes (not shown) in the other half to facilitate alignment and joining of the halves. In alternate embodiments, the two halves may be joined by a hinge, or may be separate and use features such as notches, projections, tabs, and or grooved surfaces to assist in alignment and/or securement of the halves together. In still further embodiments, the cartridge 802 may be formed as a single piece with an opening into which bone graft material, either in a loose condition or as a pre-formed pellet may be introduced.

The distal end 826 of the cartridge 802 includes sloped surfaces 814 that cooperate with the forward sloped surface 812 of the opening 810 when the cartridge 802 is positioned in the opening 810. The cartridge 802 is generally cylindrically shaped when the halves are joined, and also includes a passageway 830 that allows passage of bone graft material as well as a tamping rod. To place bone graft material into the cartridge 802, a bone graft puck 832 may be used to provide a known amount of material. The bone graft puck 832 may be broken up by a practitioner and spread around the passageway of one or both halves of the cartridge, and the cartridge halves brought together. In alternate embodiments, a pre-formed pellet may be introduced into the cartridge. In still other embodiments, loose bone graft material may be added into the cartridge. Again, such cartridges may be introduced into an inserter (or funnel) that accepts one cartridge at a time, or into a carousel or similar system that accepts more than one cartridge. Once the bone graft material has been advanced out of the cartridge 802 and deeper into the opening 810 toward the site of interest, the now empty cartridge 802 may be removed, and replaced with a full cartridge if needed. The cartridge may include a tab (not shown) or other feature to facilitate removal from the inserter 806.

In certain embodiments of the present invention, a kit is provided including a variety of sizes and/or types of funnels, and/or a variety of sizes and/or types of inserters, and/or a variety of sizes and/or types of spacers to accommodate different patients and procedures. Additionally, features of embodiments described above may generally be combined with features of other embodiments to form still additional embodiments.

In certain embodiments of the present invention, a kit is provided including a variety of sizes and/or types of funnels, and/or a variety of sizes and/or types of inserters, and/or a variety of sizes and/or types of spacers to accommodate different patients and procedures. Additionally, features of embodiments described above may generally be combined with features of other embodiments to form still additional embodiments.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A bone graft system for providing fluidic, bone graft material to a site of interest, the bone graft system comprising:
    a tamping rod;
    a bone graft cartridge containing the fluidic, bone graft material, the bone graft cartridge including a first opening and a second opening that are each sized to receive the tamping rod;
    a conduit having a first opening and a second opening, the first opening of the conduit sized to receive the tamping rod; and
    a handle associated with the first opening of the conduit, the handle including an opening sized and configured to receive the bone graft cartridge;
    wherein the tamping rod advances the fluidic, bone graft material out of the bone graft cartridge, into the first opening of the conduit, and out the second opening of the conduit to the site of interest as the tamping rod advances through the first opening and the second opening of the bone graft cartridge, through the first opening of the conduit, and into the conduit.

2. The bone graft system of claim 1, wherein the tamping rod comprises a stop configured to limit a distance that the tamping rod advances into the conduit.

3. The bone graft system of claim 1, further comprising:
    a gripping portion positioned toward the second opening of the conduit and configured to grasp and manipulate a spacer;
    wherein the second opening of the conduit is configured to direct the fluidic, bone graft material toward a leading edge of a grasped spacer such that at least a portion of the fluidic, bone graft material is separated by the leading edge of the grasped spacer and flows about the grasped spacer.

4. The bone graft system of claim 1, wherein:
    the bone graft cartridge comprises a top half and a bottom half that are movable between an open position and a closed position; and
    the bone graft cartridge, when in the open position, permits loading the top half and the bottom half with the fluidic, bone graft material.

5. The bone graft system of claim 4, wherein:
    the bone graft cartridge comprises a hinge joining the top half and the bottom half; and
    the hinge permits moving the bone graft cartridge from the open position to the closed position by folding the top half over the bottom half.

6. The bone graft system of claim 5, further comprising:
    a cartridge loader including cartridge slots that accept the bone graft cartridge;
    wherein the cartridge loader is constructed of a flexible material that permits moving the bone graft cartridge from the open position to the closed position while in the cartridge loader.

7. The bone graft system of claim 1 wherein the bone graft cartridge and the opening of the handle comprise surfaces that cooperate to limit a depth to which the bone graft cartridge is inserted into the opening of the handle.

8. The bone graft system of claim 1, wherein said bone graft cartridge contains a predetermined amount of the fluidic, bone graft material.

9. The bone graft system of claim 1, further comprising a spacer, the spacer comprising one or more surfaces adapted to disperse the fluidic, bone graft material such that the fluidic, bone graft material flows to either side of the spacer.

10. A bone graft system for delivering one or more bone graft pellets to a site of interest, the bone graft system comprising:
    a tamping rod;
    a bone graft cartridge comprising one of more cylindrical openings sized to respectively receive the one or more bone graft pellets that maintain a general, cylindrical shape during loading into the bone graft cartridge but break apart and flow about the spacer when pressed against the spacer, the bone graft cartridge including a first opening and a second opening that are each sized to receive the tamping rod;
    a conduit having a first opening and a second opening, the first opening of the conduit sized to receive the tamping rod; and
    a handle associated with the first opening of the conduit, the handling including an opening sized and configured to receive the bone graft cartridge;
    wherein the tamping rod advances the bone graft pellet out of the bone graft cartridge, into the first opening of the conduit, and out the second opening of the conduit to the site of interest as the tamping rod advances through the first opening and the second opening of the bone graft cartridge, through the first opening of the conduit, and into the conduit.

11. The bone graft system of claim 10, wherein the tamping rod comprises a stop configured to limit a distance that the tamping rod advances into the conduit.

12. The bone graft system of claim 10, further comprising:
    a gripping portion positioned toward the second opening of the conduit and configured to grasp a spacer;
    wherein the second opening of the conduit is configured to direct the bone graft pellet toward a leading edge of the spacer such that bone graft pellet breaks apart and bone graft material of the bone graft pellet flows about the spacer.

13. The bone graft system of claim 10, further comprising a spacer, the spacer comprising one or more surfaces adapted to break-up and disperse a bone graft pellet such that bone graft material comprising the bone graft pellet flows to either side of the spacer.

14. The bone graft system of claim 10, further comprising a press configured to form a bone graft pellet of the one or more bone graft pellets with a predetermined size and shape.

15. The bone graft system of claim 14, wherein said press comprises a slot configured to accept bone graft material and form bone graft material into a bone graft pellet of the one or more bone graft pellets with a pre-determined size and shape.

16. The bone graft system of claim 15, wherein the bone graft press comprises a top and a bottom joined by a hinge.

17. A bone graft system according to claim 10, wherein said bone graft cartridge comprises a carousel that is configured to accept a plurality of bone graft pellets.

18. The bone graft system according to claim 10, wherein said bone graft cartridge comprises a magazine that is sized to sequentially receive a plurality of bone graft pellets.

\* \* \* \* \*